US008532769B2

(12) United States Patent
Kornet et al.

(10) Patent No.: US 8,532,769 B2
(45) Date of Patent: Sep. 10, 2013

(54) HEART RATE VARIABILITY DISTINCTION

(75) Inventors: Lilian Kornet, Maastricht (NL);
Hans-Juergen Bruns, Muenster (DE);
Raphael Schneider, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 578 days.

(21) Appl. No.: 12/610,009

(22) Filed: Oct. 30, 2009

(65) Prior Publication Data

US 2011/0105926 A1 May 5, 2011

(51) Int. Cl.
*A61N 1/00* (2006.01)
(52) U.S. Cl.
USPC .................................................. 607/17
(58) Field of Classification Search
USPC ..................... 607/9–32; 600/508–528
See application file for complete search history.

(56) References Cited

U.S. PATENT DOCUMENTS

| | | | |
|---|---|---|---|
| 5,117,824 A | | 6/1992 | Keimel et al. |
| 5,480,412 A | * | 1/1996 | Mouchawar et al. ............. 607/6 |
| 5,609,156 A | | 3/1997 | Keith et al. |
| 5,704,365 A | * | 1/1998 | Albrecht et al. ............. 600/515 |
| 5,749,900 A | * | 5/1998 | Schroeppel et al. ............. 607/4 |
| 5,957,855 A | | 9/1999 | Oriol et al. |
| 6,922,585 B2 | | 7/2005 | Zhou et al. |
| 7,010,345 B2 | | 3/2006 | Hill et al. |
| 7,139,607 B1 | | 11/2006 | Shelchuk |
| 2002/0128563 A1 | | 9/2002 | Carlson et al. |
| 2004/0133115 A1 | * | 7/2004 | Hamilton et al. ............. 600/511 |
| 2004/0193066 A1 | * | 9/2004 | Carlson et al. ............. 600/509 |
| 2005/0137489 A1 | | 6/2005 | Jackson et al. |
| 2006/0161208 A1 | | 7/2006 | Pastore et al. |

OTHER PUBLICATIONS

Search Report and Written Opinion from corresponding PCT Application Serial No. PCT/US2010/033354 dated Jul. 7, 2010 (11 pages).
Axel Bauer et al., "Deceleration capactity of heart rate as a predictor of mortality after myocardial infarction: cohort study," *Lancet*, 367, May 20, 2006 (pp. 1674-1681).
Lie Gao et al., "Cardiac sympathetic afferent stimulation impairs baroreflex control of renal sympathetic nerve activity in rats," *Am J Physiol Heart Circ Physiol* 286:H1706-H1711 (2004).
Federico Lombardi et al., "Sudden cardiac death: role of heart rate variability to identify patients at risk," *Cardiovascular Research* 50 (2001) 210-217.

(Continued)

*Primary Examiner* — Christopher D Koharski
*Assistant Examiner* — Nadia Ahmad
(74) *Attorney, Agent, or Firm* — Michael C. Soldner

(57) ABSTRACT

Systems, methods and devices for monitoring, analyzing, and processing a patient's heart rate signal for HRV characteristics are described herein. A first heart rate signal is acquired. The first heart rate signal includes at least one indication of an interval duration of cardiac activity. At least one accelerating portion and at least one decelerating portion of the first heart rate signal are identified. An average heart rate signal is acquired. The accelerating portion or the decelerating portion of the first heart rate signal is replaced with the average heart rate signal to produce a second heart rate signal. A frequency spectrum of the second heart rate signal may be obtained and utilized to predict or detect one or more autonomic conditions of a patient. Therapy may initiated or titrated in response to prediction or detection of the autonomic condition.

27 Claims, 17 Drawing Sheets

(56) References Cited

OTHER PUBLICATIONS

R. Moore et al., "Altered short term heart rate variability with spinal cord stimulation in chronic refractory angina: evidence for the presence of procedure related cardiac sympathetic blockade," *Heart* 2004; 90; 211-212.

Vladimir Shusterman, MD, PhD et al., "Autonomic Nervous System Activity and the Spontaneous Initiation of Ventricular Tachycardia," *JACC*, vol. 32, No. 7 (Dec. 1998) pp. 1891-1899.

Rong Zhang et al., "Transfer function analysis of dynamic cerebral autoregulation in humans," *Am J Physiol Heart Circ Physiol*, 274:H233-H241 (1998).

William H. Wehrmacher et al., "The Unbalanced Heart Animal Models of Cardiac Dysrhythmias," *Cardiology*, 64:65-74 (1979).

Reply to Written Opinion for international application No. PCT/US2010/033354, filed Aug. 23, 2011, 6 pp.

Reply to Written Opinion dated Oct. 31, 2011, from international application No. PCT/US2010/033354, filed Nov. 30, 2011, 16 pp.

International Preliminary Report on Patentability from corresponding PCT Application Serial No. PCT/US2010/033354 dated Jan. 25, 2012 (11 pages).

Written Opinion of the International Preliminary Examining Authority from corresponding PCT Application Serial No. PCT/US2010/033354 dated Oct. 31, 2011, (5 pages).

\* cited by examiner

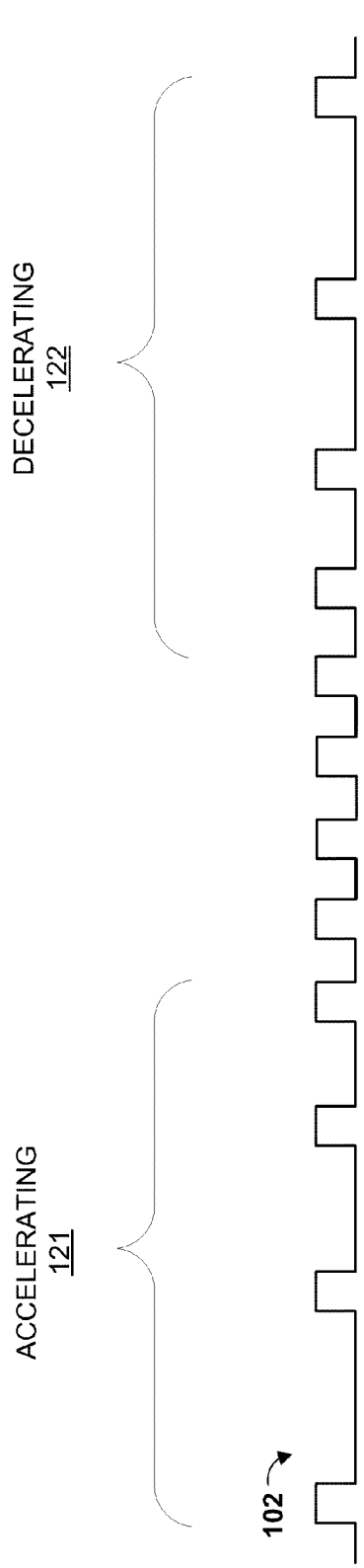
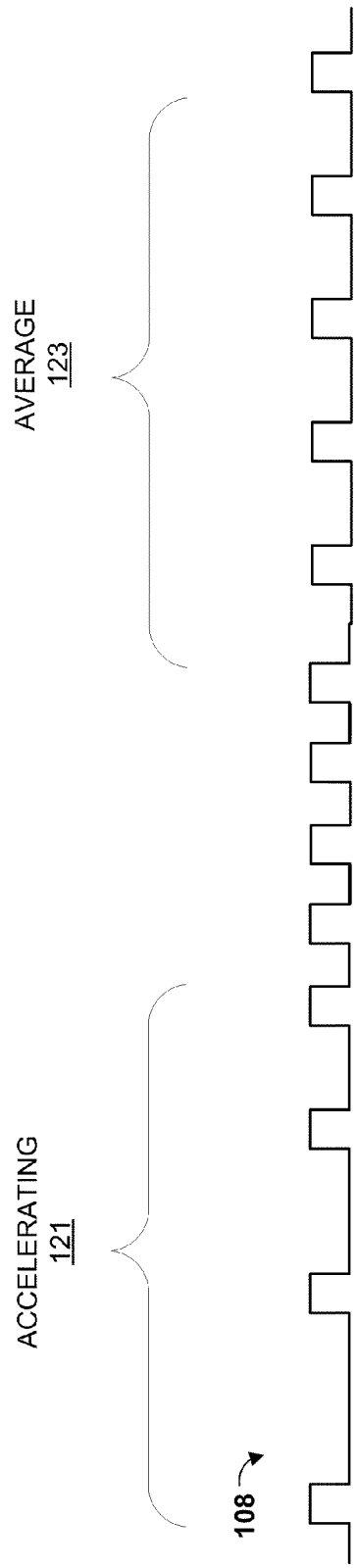
FIG. 11A
FIG. 11B

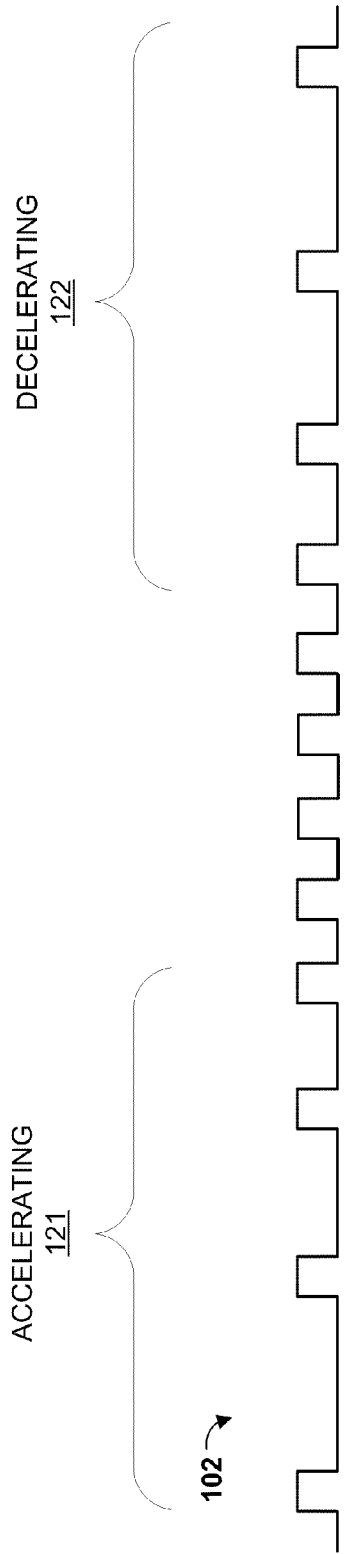
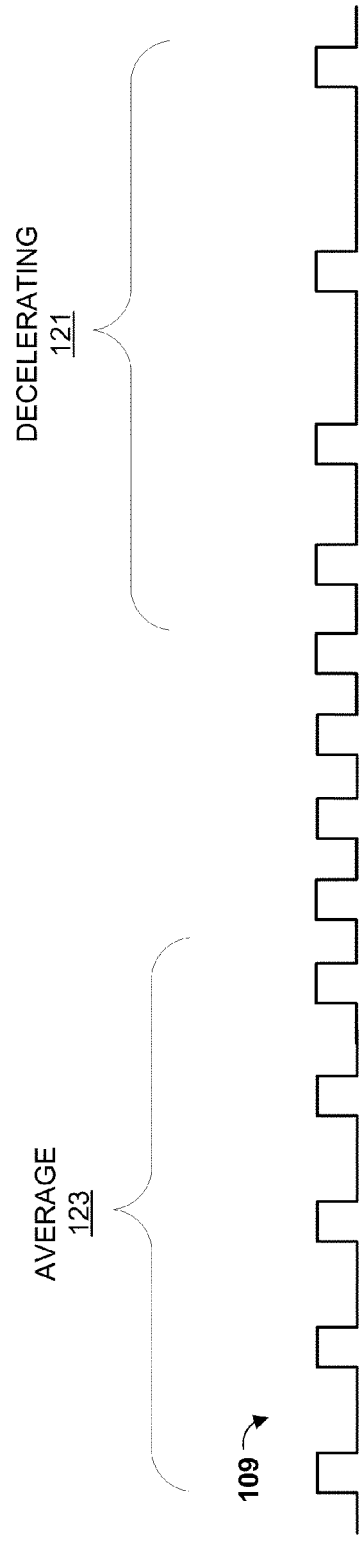
FIG. 12A
FIG. 12B

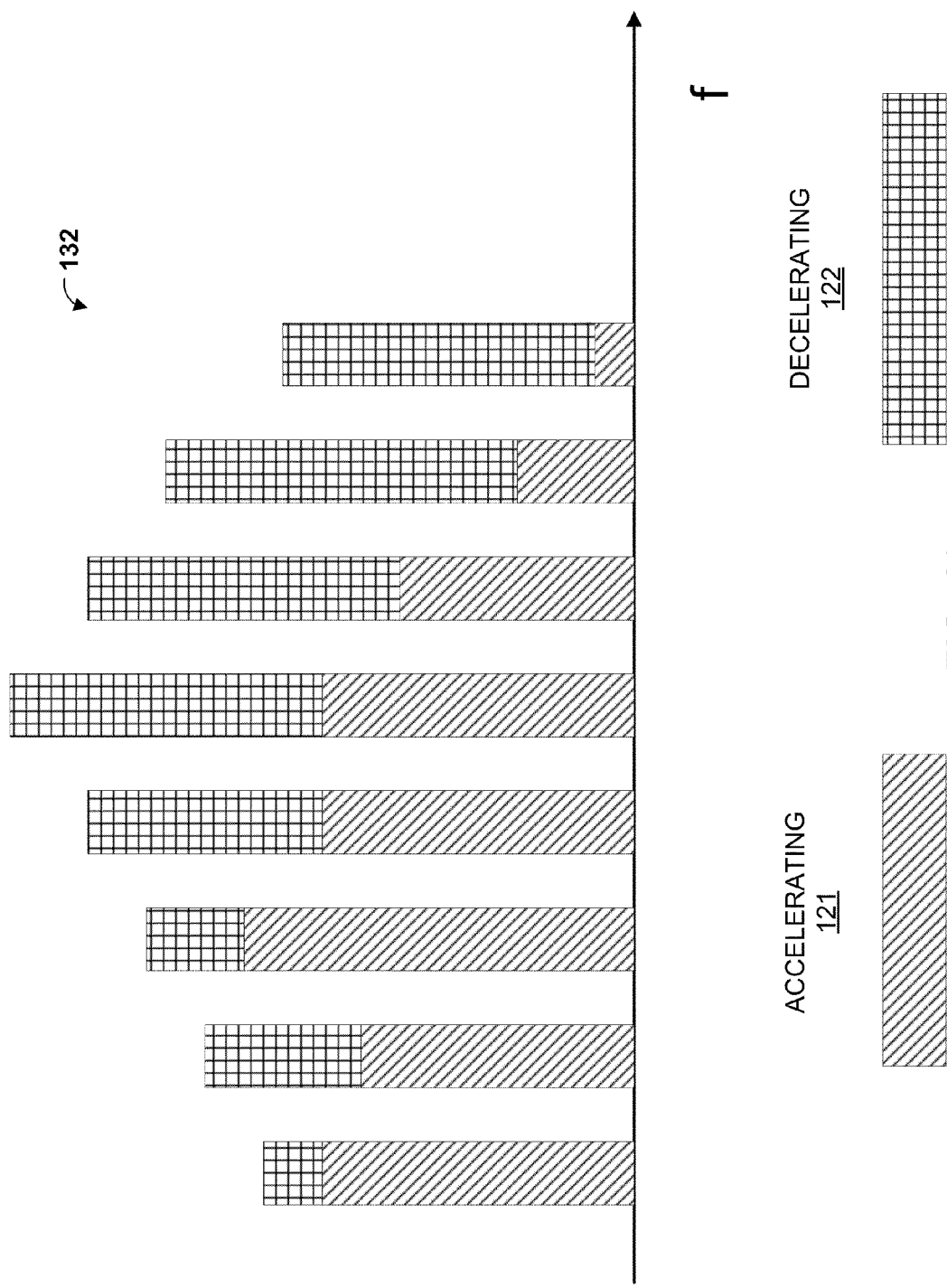

HEART RATE VARIABILITY DISTINCTION

TECHNICAL FIELD

The invention relates to monitoring and analysis of autonomic indicators. More specifically, this invention relates to the monitoring and analysis of Heart Rate Variability (HRV).

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissue. Some therapies include the delivery of electrical stimulation to such organs or tissues. Others include the delivery of one or more drugs within or outside of a patient's body.

Some medical devices include one or more electrodes for the delivery of electrical stimulation to such organs or tissues and/or for sensing various indications of patient health. Some medical devices include electrodes to sense intrinsic electrical signals of the heart, and/or other sensors for sensing various physiological parameters of a patient. Some medical devices include sensors for sensing mechanical contractions of the heart.

In some cases, a medical device senses one or more indications of cardiac cycles, e.g. a rate of intrinsic depolarizations, repolarizations, and or contractions of a patient's heart. One or more heart rate signals may be acquired based on the sensed indications. Heart signals may include indications of frequency, amplitude, or other aspects of the functioning of a patient's heart. A heart rate signal may be acquired based on sensing of intrinsic electrical signals, e.g. an EKG or ECG signal. A heart rate signal may also be acquired based on sensing of pressure signals, audio signals, force signals, motion signals, or any other means for detecting at last one signal indicative of a patient's cardiac activity, alone or in combination.

Various characteristics of a heart rate signal may be processed and/or analyzed by an internal or external medical device, physician, or other user to determine one or more autonomic conditions of a patient. One example of a heart rate signal characteristic is Heart Rate Variability (HRV). HRV is a rate at which a heartbeat changes in time. HRV may have attributes including amplitude, frequency, average heartbeat rate, and coherence. HRV attributes may be indicative of functioning of a patient's autonomic nervous system. Changes in autonomic function may indicate one or more autonomic conditions of a patient. Autonomic conditions may also be related to hemodynamic conditions of the patient. Some examples of hemodynamic conditions that may be indicated by autonomic attributes include increased risk of coronary heart disease (CHD), cardiovalscular disease mortality (CVD), or a risk of arrhythmia.

SUMMARY

In general, the disclosure is directed to techniques for monitoring HRV. One or more heart rate signals may be processed to isolate accelerating or decelerating portions, respectively, of a heart rate signal. In some cases, one or more heart rate signals may be translated into the frequency domain to create an autonomic tone signal for analysis or further processing. In some examples, the accelerated and/or decelerated portions of the heart rate signal are isolated for separate analysis. The one or more heart rate signals may be used to monitor HRV characteristics of a patient's heart rate to predict or detect one or more autonomic conditions of a patient. The one or more autonomic conditions may be related to hemodynamic conditions of the patient. For example, the one or more heart rate signals may be used to predict or detect cardiovascular disease and/or arrhythmia conditions in a patient. One or more therapies may be initiated or titrated (adjusted) in response to prediction or detection of an autonomic condition of the patient.

More particularly, in one example a method for monitoring HRV is described herein. The method includes acquiring a first heart rate signal that includes an indication of at least one interval duration of a heart rate of a patient. The method further includes identifying at least one accelerating portion of the first heart rate signal for which the heart rate is increasing. The method further includes identifying at least one decelerating portion of the first heart rate signal for which the heart rate is decreasing. The method further includes determining an average heart rate signal. The method further includes replacing, in the first heart rate signal, one of the accelerating portion or the decelerating portion with the average heart rate signal to produce a second heart rate signal.

In another example, a system that monitors HRV is described herein. The system includes a medical device. The system further includes at least one sensor coupled to the medical device that detects at least one indication of a cardiac cycle of a patient. The system further includes a processor configured to acquire, based on detection by the sensor of at least one indication of a cardiac cycle, at least one first heart rate signal that includes at least one indication of an interval duration. The processor is further configured to identify at least one accelerating portion of the first heart rate signal for which the heart rate is increasing. The processor is further configured to identify at least one decelerating portion of the first heart rate signal for which the patient's heart rate is decreasing. The processor is further configured to determine an average heart rate signal. The processor is further configured to replace, in the first heart rate signal, one of the accelerating portion or the decelerating portion with the average heart rate signal to produce a second heart rate signal.

In another example, a computer-readable medium comprising instructions for causing a programmable processor to acquire a first heart rate signal that includes an indication of at least one interval duration of a heart rate of a patient. The computer-readable medium further comprises instructions for causing the programmable processor to identify at least one accelerating portion of the first heart rate signal for which the heart rate is increasing. The computer-readable medium further comprises instructions for causing the programmable processor to identify at least one decelerating portion of the first heart rate signal for which the heart rate is decreasing. The computer-readable medium further comprises instructions for causing the programmable processor to determine an average heart rate signal. The computer-readable medium further comprises instructions for causing the programmable processor to replace, in the first heart rate signal, one of the accelerating portion or the decelerating portion with the average heart rate signal to produce a second heart rate signal.

The details of one or more examples are set forth in the accompanying drawings and the description below. Other features, objects, and advantages of the invention will be apparent from the description and drawings, and from the claims.

BRIEF DESCRIPTION OF DRAWINGS

FIGS. 11A and 11B depict an example of a first heart rate signal and an accelerating second heart rate signal consistent with the disclosure.

FIGS. 12A and 12B depict an example of a first heart rate signal and a decelerating second heart rate signal consistent with this disclosure.

FIG. 13 depicts an example frequency response of a first heart rate signal consistent with this disclosure.

DETAILED DESCRIPTION

Figure 1:
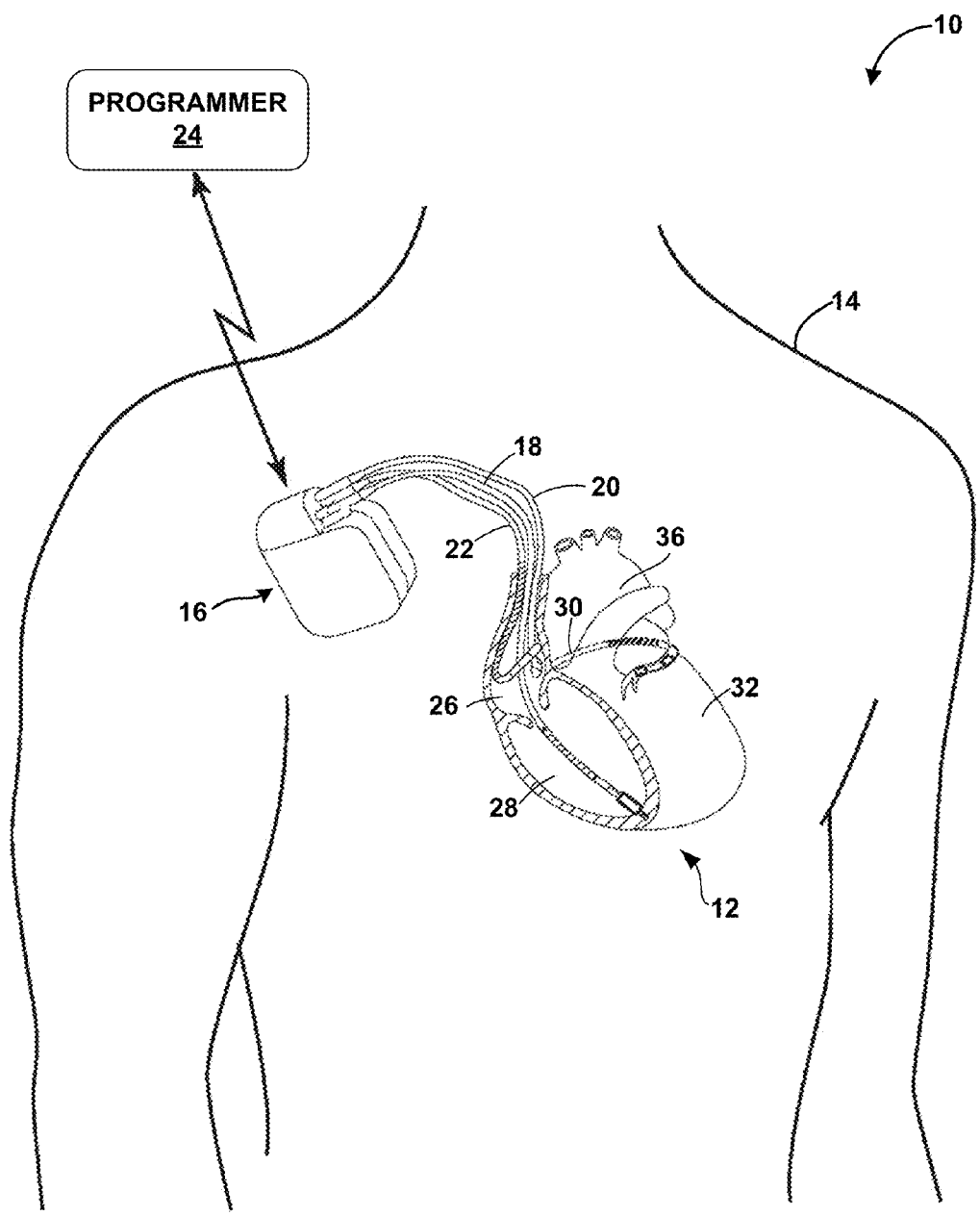
FIG. 1 depicts one specific example of a therapy system.

FIG. 1 is a conceptual diagram illustrating an example system 10 that may be used for sensing of physiological parameters of patient 14 and/or to provide therapy to heart 12 of patient 14. System 10 depicted in FIG. 1 is provided as only one example of a system that may be utilized according to the disclosure described herein. One of skill in the relevant art will recognize that the disclosure described herein may be utilized with systems that include any combination of internal medical devices, external medical devices, internal or external leads and/or electrodes, programmers, physicians, or other users.

Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. In addition to providing electrical signals to heart 12, IMD 16 may also provide therapy in the form of electrical signals to other portions of the body, e.g. neurological therapy that provides electrical stimulation to and/or monitors conditions associated with the brain, spinal cord, or other neural tissue of patient 14. IMD 16 may also be adapted to deliver drugs internally or externally of a patient to provide one or more drug based therapies. Further, therapy system 10 may include a single medical device 16, or multiple internal or external medical devices for specific purposes, e.g. a first medical device to deliver electrical therapy, a second medical device to deliver drug therapy, and/or a third medical device to deliver neurological therapy. Therapy system 10 may further include one or more additional medical devices adapted for sensing various hemodynamic, autonomic, or other conditions, e.g. blood sensors, temperature sensors, patient activity sensors, force sensors, blood flow sensors or any other sensor adapted to sense one or more hemodynamic, autonomic, or other indications internal or external to a patient 14.

FIG. 1 depicts one specific example of a therapy system 10 for exemplary purposes. Other configurations are also contemplated and consistent with the disclosure described herein. In the example of FIG. 1, leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, therapy system 10 may additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, therapy system 10 may additionally or alternatively include temporary or permanent epicardial or subcutaneous leads, instead of or in addition to transvenous, intracardiac leads 18, 20 and 22. Such leads may be used for one or more of cardiac sensing, pacing, or cardioversion/defibrillation. Additionally, in some examples, an IMD need not be coupled to leads, and instead itself includes a plurality of electrodes, which may be formed on or integrally with a housing of the IMD. An example of such an IMD is the Reveal® monitor, which is commercially available from Medtronic, Inc. of Minneapolis, Minn.

IMD 16 may sense electrical signals attendant to the depolarization and repolarization of heart 12 via electrodes (not shown in FIG. 1) coupled to at least one of the leads 18, 20, 22. Electrodes may also be disposed at one or more locations at a housing of IMD 16. Electrodes may also be external to a patient, and also may included in one or more additional IMDs, e.g. a dedicated sensor IMD.

System 10 may include system programmer 24. Programmer 24 may comprise a handheld computing device, computer workstation, or networked computing device. Programmer 24 may include a user interface that receives input from a user, e.g. physician or other caregiver. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD 16 to initiate or titrate (adjust) therapy provided by the IMD 16. The term titrate as utilized herein is intended to encompass any adjustment to a therapy provided by a medical device, e.g. IMD 16, including adjustment of cardiac or neurological electrical stimulus therapy, drug therapy, or the like.

For example, the user may use programmer 24 to retrieve information from IMD 16 regarding heart 12 activity (e.g., a patient's heart rate), including trends therein over time. As another example, the user may use programmer 24 to retrieve information from IMD 16 regarding changes in HRV, such as changes in accelerating or decelerating components of HRV, determined using any of the techniques described herein. As another example, the user may use programmer 24 to retrieve information from IMD 16 regarding other sensed physiological parameters of patient 14, such as intracardiac or intravascular pressure, activity, posture, respiration, or thoracic impedance. In some examples, this information may be presented to the user as an alert. For example, heart rate related condition identified based on a detected heart rate signal may trigger IMD 16 to transmit an alert to the user via programmer 24.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
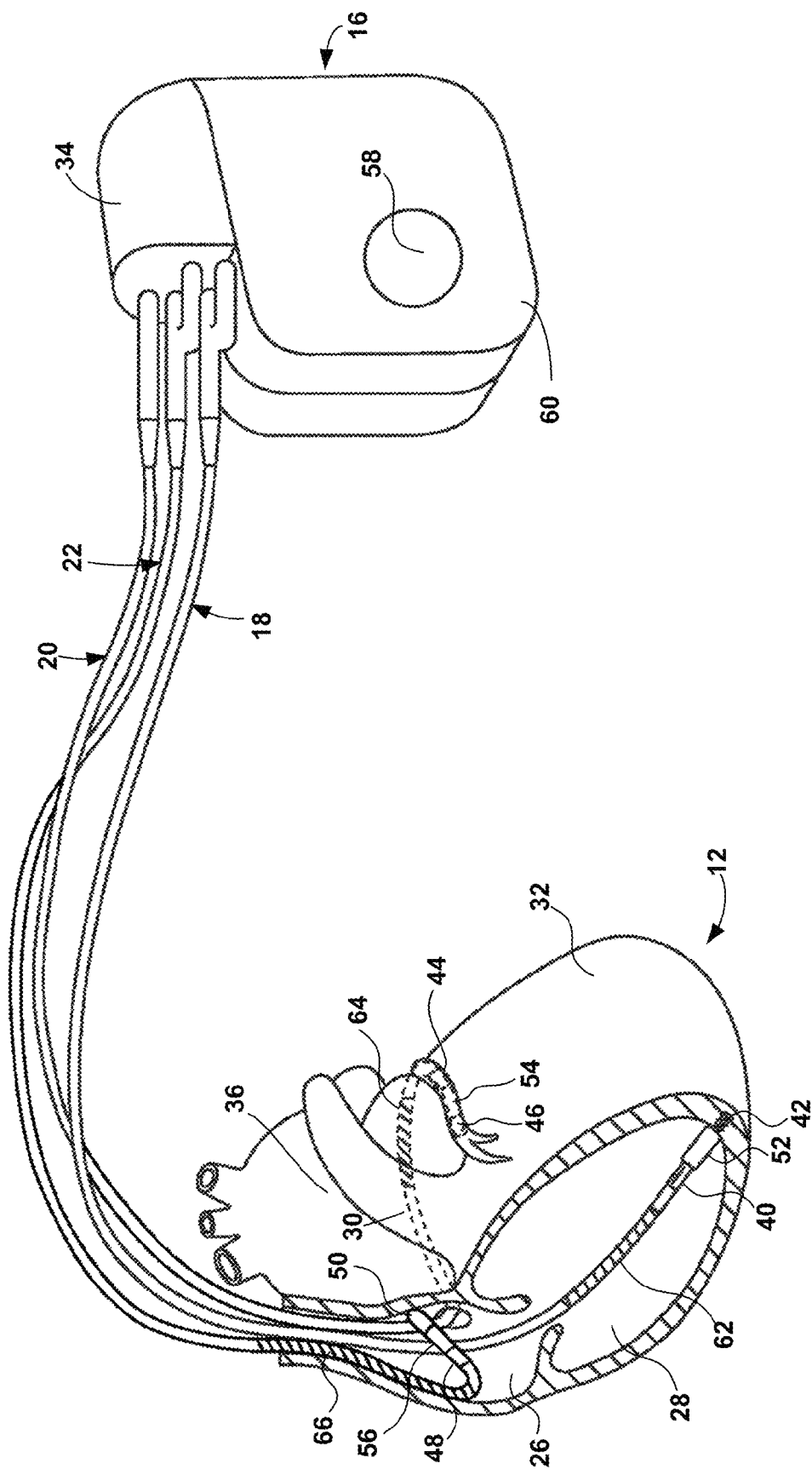
FIG. 2 depicts one specific example of a therapy system in detail.

FIG. 2 is a conceptual diagram illustrating IMD 16 and leads 18, 20 and 22 of therapy system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. A combination of electrodes used for sensing may be referred to as a sensing configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. Other examples of therapy systems may include a single lead that extends from IMD 16 into right atrium 26 or right ventricle 28, or two leads that extend into a respective one of the right ventricle 28 and right atrium 26. Any electrodes located on these additional leads may be used in sensing and/or stimulation configurations.

Additionally, as previously mentioned, IMD 16 need not included leads, and also need not deliver therapy to heart 12. In general, this disclosure may be applicable to any implantable or external medical device configured to sense a physiological signal indicative of the electrical or mechanical activity of the heart.

Figure 3:
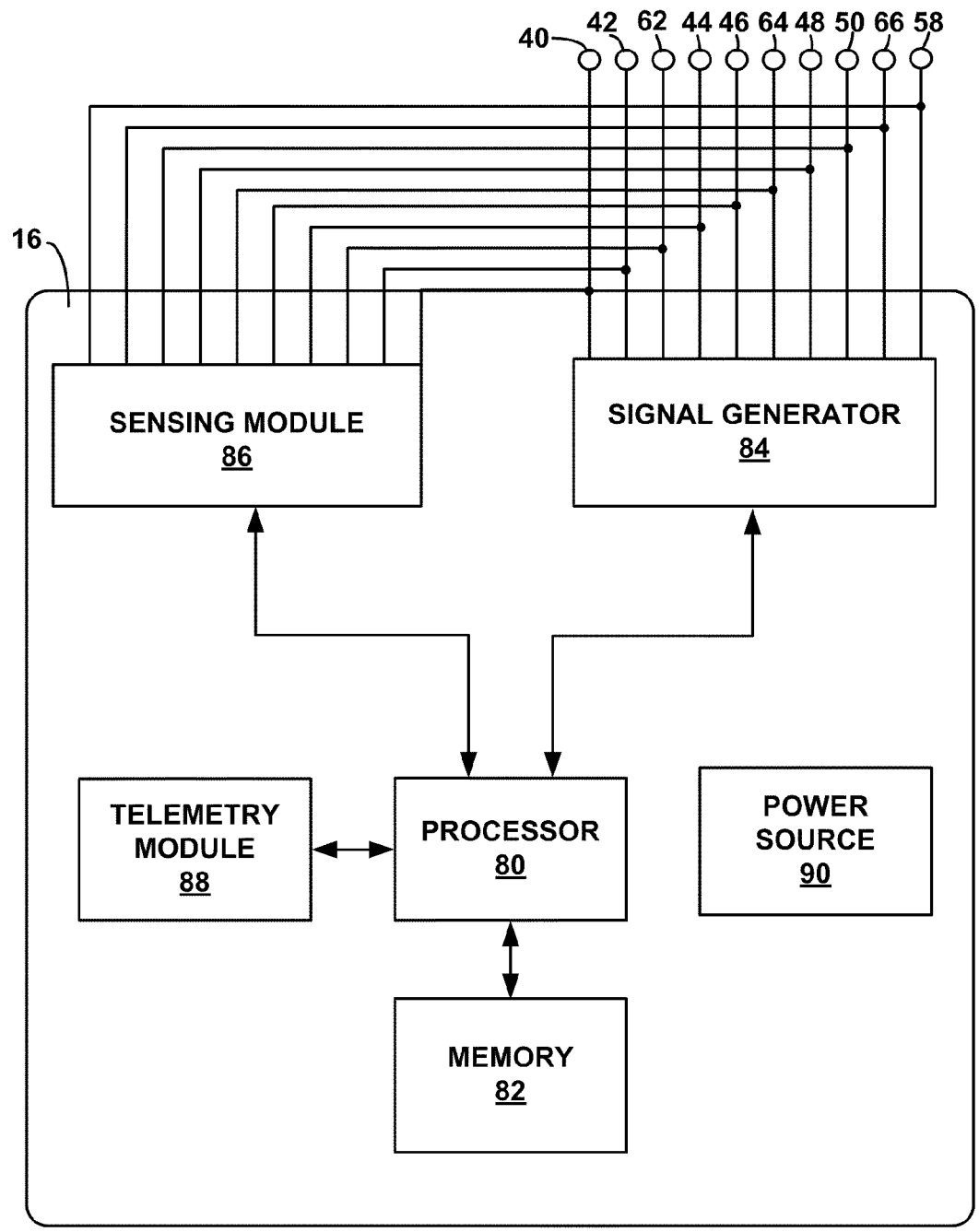
FIG. 3 is a functional block diagram illustrating one example of a configuration of an implantable medical device.

FIG. 3 is a functional block diagram illustrating an example configuration of IMD 16. In the illustrated example, IMD 16 includes a processor 80, memory 82, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 may control signal generator 84 to deliver stimulation therapy to heart 12 according to a selected one or more of therapy programs, which may be stored in memory 82. For example, processor 80 may control stimulation generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Sensing module 86 may also include a switch module to select which of the available electrodes are used to sense the heart activity, depending upon which electrode combination is used in the current sensing configuration. In some examples, processor 80 may select the electrodes that function as sense electrodes, i.e., select the sensing configuration, via the switch module within sensing module 86. Processor 80 may control the functionality of sensing module 86 by providing signals via a data/address bus.

Sensing module 86 may include one or more detection channels, each of which may comprise an amplifier. The detection channels may be used to sense cardiac signals. Some detection channels may detect events, such as R- or P-waves, and provide indications of the occurrences of such events to processor 80. One or more other detection channels may provide the signals to an analog-to-digital converter, for processing or analysis by processor 80. In response to the signals from processor 80, the switch module within sensing module 86 may couple selected electrodes to selected detection channels.

Processor 80 may maintain one or more intervals counters. For example, if IMD 16 is configured to generate and deliver pacing pulses to heart 12, processor 80 may maintain programmable counters which control the basic time intervals associated with various modes of pacing. Intervals defined by processor 80 may include atrial and ventricular pacing escape intervals, refractory periods during which sensed P-waves and R-waves are ineffective to restart timing of the escape intervals, and the pulse widths of the pacing pulses. As another example, processor 80 may define a blanking period, and provide signals sensing module 86 to blank one or more channels, e.g., amplifiers, for a period during and after delivery of electrical stimulation to heart 12. The durations of these intervals may be determined by processor 80 in response to stored data in memory 82. Processor 80 may also determine the amplitude of the cardiac pacing pulses.

Interval counters maintained by processor 80 may be reset upon sensing of R-waves and P-waves with detection channels of sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In examples configured for delivery of pacing pulses, processor 80 may also reset the interval counters upon the generation of pacing pulses by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, PR intervals and R-P intervals, which are measurements that may be stored in memory 82. Processor 80 may process the count in the interval counters to identify one or more autonomic conditions as discussed in further detail below. A portion of memory 82 may be configured as a plurality of recirculating buffers, capable of holding series of measured intervals, which may be analyzed by processor 80 to determine whether the patient's heart 12 is presently exhibiting one or more autonomic conditions.

In some examples, processor 80 may identify one or more R-R (or P-P, or other) interval durations (time period between identified R-waves, P-waves, or other component of a detected ECG signal). The one or more interval durations may be detected for a certain number of consecutive cycles, for a certain percentage of cycles within a running window, or a running average for a certain number of cardiac cycles, as examples.

Although not illustrated in FIG. 3, IMD 16 may include or be coupled to any of a variety of other sensors that provide a signal that varies as a function of a physiological parameter of the patient. In some examples, the signals vary as a function of the mechanical contraction of heart 12. Examples of sensors that provide signals that vary as a function of the mechanical contraction of the heart include pressure sensors, such as capacitive pressure sensors, accelerometers, and piezoelectric elements. Such sensors may located on one or more of leads 18, 20, 22, or another lead, or may be part of a separate device implanted on or in the heart, or otherwise implanted within patient 14.

Sensing module 86 and/or processor 80 may analyze the signals from such mechanical contraction sensors, instead of or in addition to the electrical signals of heart 16 provided by electrodes as described above, to identify cardiac cycle intervals. For example, sensing module or processor 80 may identify the occurrence of cardiac contractions based on the signals, and processor 80 may determine the cardiac cycle intervals between the cardiac contractions. Accordingly, although the techniques for evaluating HRV described herein are described primarily with reference to examples in which intervals between electrical cardiac events are analyzed, the techniques may be employed to analyze cardiac cycle intervals that are determined based on mechanical cardiac contractions.

Figure 4:
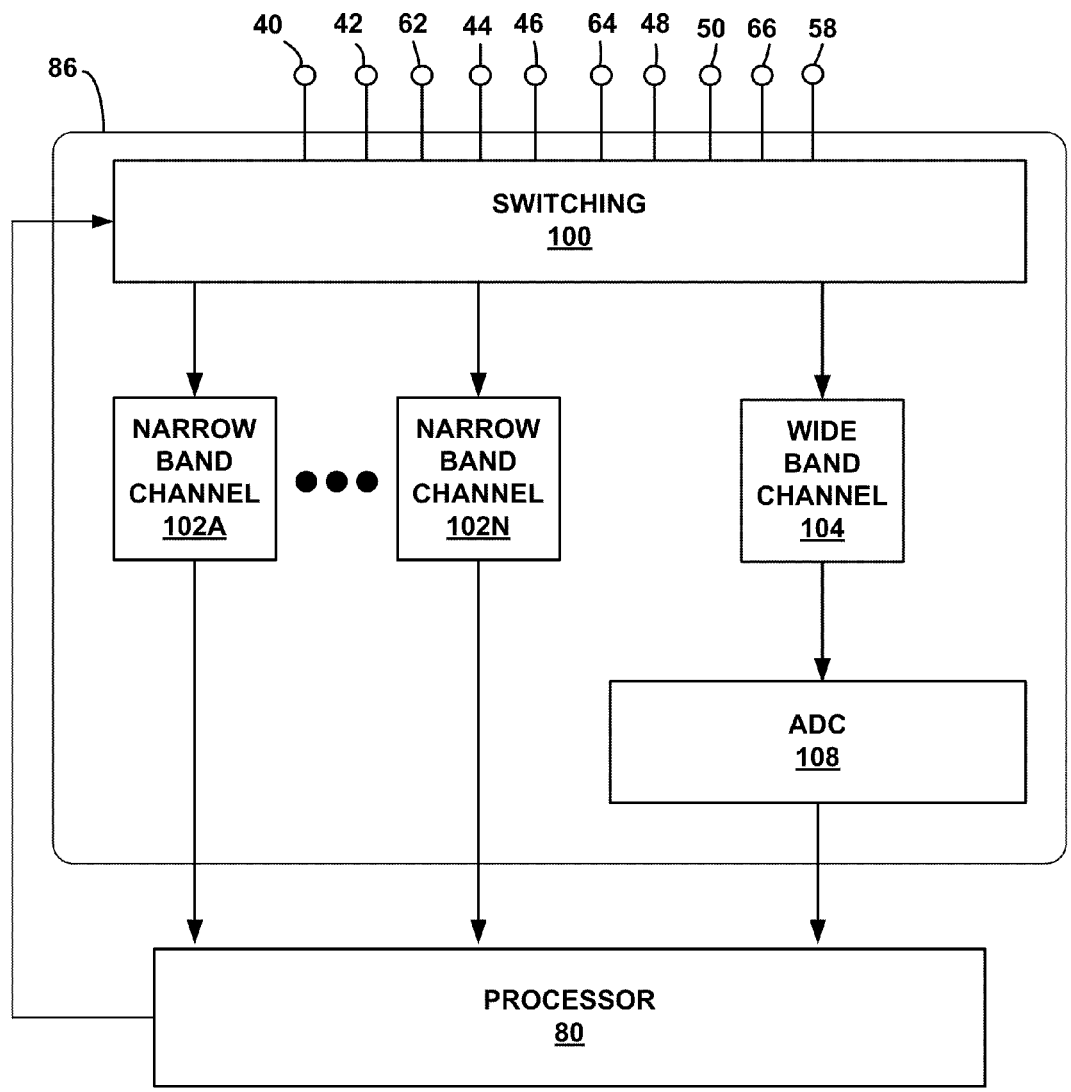
FIG. 4 is a block diagram of an example configuration of an electrical sensing module.

FIG. 4 is a block diagram of an example configuration of electrical sensing module 86. As shown in FIG. 4, electrical sensing module 86 includes multiple components including a switching module 100, narrow band channels 102A to 102N (collectively "narrow band channels 102"), wide band channel 104, and analog to digital converter (ADC) 108. Switching module 100 may, based on control signals from processor 80, control which of electrodes 40, 42, 44, 46, 48, 50, 58, 62, 64 and 66 is coupled to which of channels 102 and 104 at any given time.

Each of narrow band channels 102 may comprise a narrow band filtered sense-amplifier that compares the detected signal to a threshold. If the filtered and amplified signal is greater than the threshold, the narrow band channel indicates that a certain electrical heart event has occurred. Processor 80 then uses that detection in measuring frequencies of the detected events. Narrow band channels 102 may have distinct functions. For example, some various narrow band channels may be used to detect either atrial or ventricular events.

In one example, at least one narrow band channel 102 may include an R-wave amplifier that receives signals from the sensing electrode configuration of electrodes 40 and 42, which are used for sensing and/or pacing in right ventricle 28 of heart 12. Another narrow band channel 102 may include another R-wave amplifier that receives signals from the sensing electrode configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel 102 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

Wide band channel 104 may comprise an amplifier with a relatively wider pass band than the R-wave or P-wave amplifiers. Signals from the sensing electrode configuration that is selected for coupling to this wide-band amplifier may be converted to multi-bit digital signals by ADC 108. In some examples, processor 80 may store digitized versions of signals from wide band channel 104 in memory 82 as one or more electrocardiograms (EGMs).

In some examples, processor 80 may employ digital signal analysis techniques to characterize the digitized signals from wide band channel 104 to, for example, detect and classify the patient's heart rhythm. Processor 80 may detect and classify the patient's heart rhythm by employing any of the numerous signal processing methodologies known in the art. In one example, processor 80 may detect, process, and/or classify a patient's heart rhythm based on indications from one or more narrow band channels 102 to determine a heart rate signal including at least one indication of an interval duration. Further, in some examples, processor 80 may analyze the morphology of the digitized signals from wide band channel 104 to distinguish between noise and cardiac depolarizations.

Figure 5:
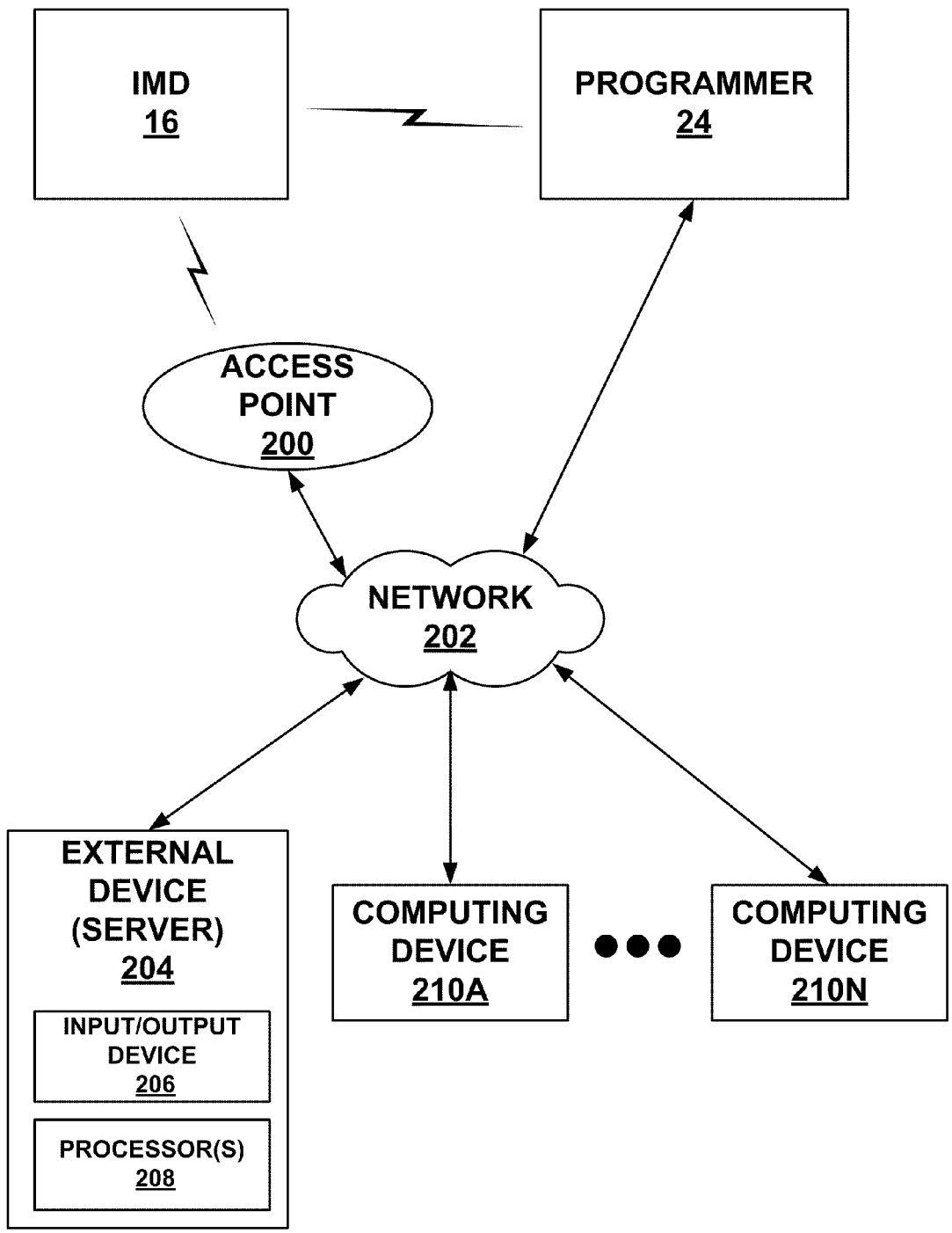
FIG. 5 is a block diagram illustrating an example system that includes an external device, such as a server, and one or more computing devices, that are coupled to a medical device and programmer shown via a network.

FIG. 5 is a block diagram illustrating an example system that includes an external device, such as a server 204, and one or more computing devices 210A-210N, that are coupled to an IMD 16 and programmer 24 shown in FIG. 1 via a network 202. The system of FIG. 5 is shown with an internal medical device 16 utilized to capture, process, and/or communicate with other components of the system. However, the use of external medical devices is also contemplated and consistent with the disclosure provided herein.

In the example of FIG. 5, IMD 16 may use its telemetry module 88 to communicate with programmer 24 via a first wireless connection, and to communication with an access point 200 via a second wireless connection. In the example of FIG. 5, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other embodiments, access point 200 may be coupled to network 202 through different forms of connections, including wired or wireless connections. In some embodiments, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some embodiments, server 204 or computing devices 210 may control or perform any of the various functions or operations described herein, e.g., perform signal processing techniques, detect one or more autonomic conditions of a patient, and/or control therapy initiation or modification of therapy delivery in response to a detected autonomic condition consistent with this disclosure.

In some cases, server 204 may be configured to provide a secure storage site for archival of information that has been collected from IMD 16 and/or programmer 24. Network 202 may comprise a local area network, wide area network, or global network, such as the Internet. In some cases, programmer 24 or server 204 may assemble information in web pages or other documents for viewing by trained professionals, such as clinicians, via viewing terminals associated with computing devices 210. The system of FIG. 5 may be implemented, in some aspects, with general network technology and functionality similar to that provided by the Medtronic CareLink® Network developed by Medtronic, Inc., of Minneapolis, Minn.

As discussed above, any component of the system depicted in FIG. 5 may be adapted to perform signal processing functionality consistent with the disclosure provided herein. Accordingly, the term processor 80 as described herein may be comprised of a single processor device or module of any component of the system of FIG. 5. The term processor may instead be comprised of any combination of single or multiple processor devices or modules shared between multiple components of the system of FIG. 5, for example IMD 16, programmer 24, access point 200, external device (server) 204, computing devices 210A-N, one or more external medical devices (not depicted), any other external device or circuitry (e.g. a spectrum analyzer), or any other device or combination of devices capable of signal processing consistent with the disclosure described herein.

As discussed above, IMD 16 may be adapted to sense and/or identify one or more indications of intrinsic polarization and/or depolarization of a patient's heart (also know as one or more cardiac cycles). In doing so, IMD 16 may create at least one heart rate signal that includes at least one indication of an interval duration, or a timing of sequential cardiac cycles.

Figure 6:
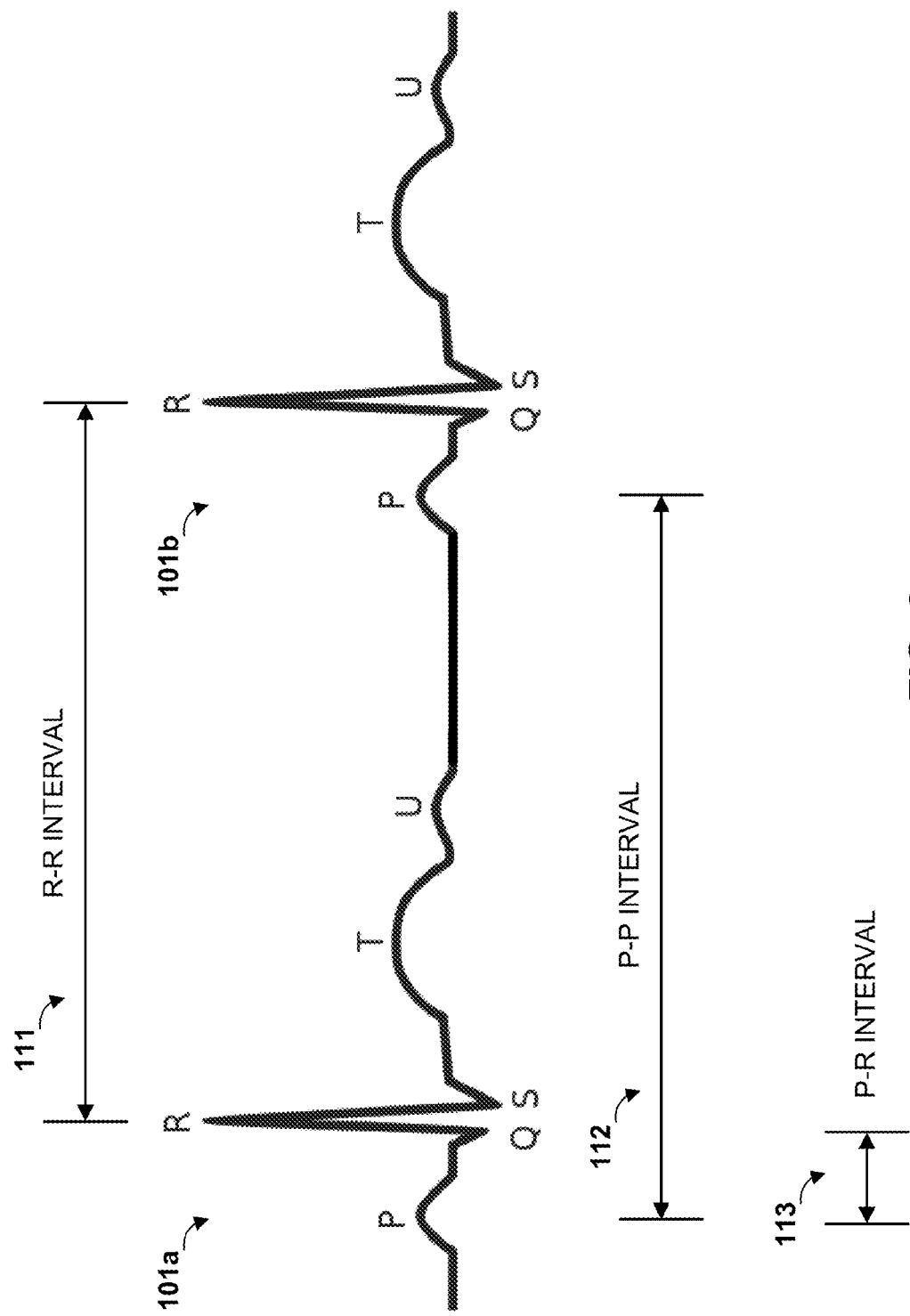
FIG. 6 depicts one example of an ECG signal consistent with this disclosure.

FIG. 6 shows one example of an ECG signal that may be sensed by an IMD 16 as described above. As depicted, each individual cardiac cycle 101a, 101b within ECG signal includes distinguishable characteristics. For example, the cardiac cycles of FIG. 6 include P, Q, R, S, T and U waves or characteristics. One or more of these ECG signal characteristics may be processed and/or analyzed to determine one or more indications of a patient's health, for example to determine at least one interval duration and/or to determine at least one heart rate signal that includes at least one indication of at least one duration interval.

IMD 16 may be adapted to detect an occurrence of an R-wave of an ECG signal that represents a cardiac cycle by one or more sense amplifiers as discussed above with respect to FIGS. 3 and 4. R-waves may be utilized by IMD 16 to determine one or more interval durations that represent a timing of cardiac cycles. In one example, an interval duration may be determined based on an R-R interval 111, or an amount to time between detection of consecutive R-waves as shown in FIG. 6. Other characteristics of an ECG signal may instead be detected for the purpose of determining an interval duration, for example a P-P interval 112 or a P-R interval 113 as also depicted in FIG. 6.

In some cases, a patient's heart rate may include interval durations that are longer or shorter than others. As discussed in further detail below, interval durations of a patient's heart rate may be processed and/or analyzed, and variations in intervals durations, also referred to as Heart Rate Variability (HRV), may be utilized by an internal or external medical device, physician, or other user to predict or detect one or more autonomic conditions of a patient. In addition, in response to detection, processing, and/or analysis of HRV of a patient's heart rate, one or more various therapies may be initiated or titrated to remedy or improve one or more detected autonomic conditions.

Figure 7:
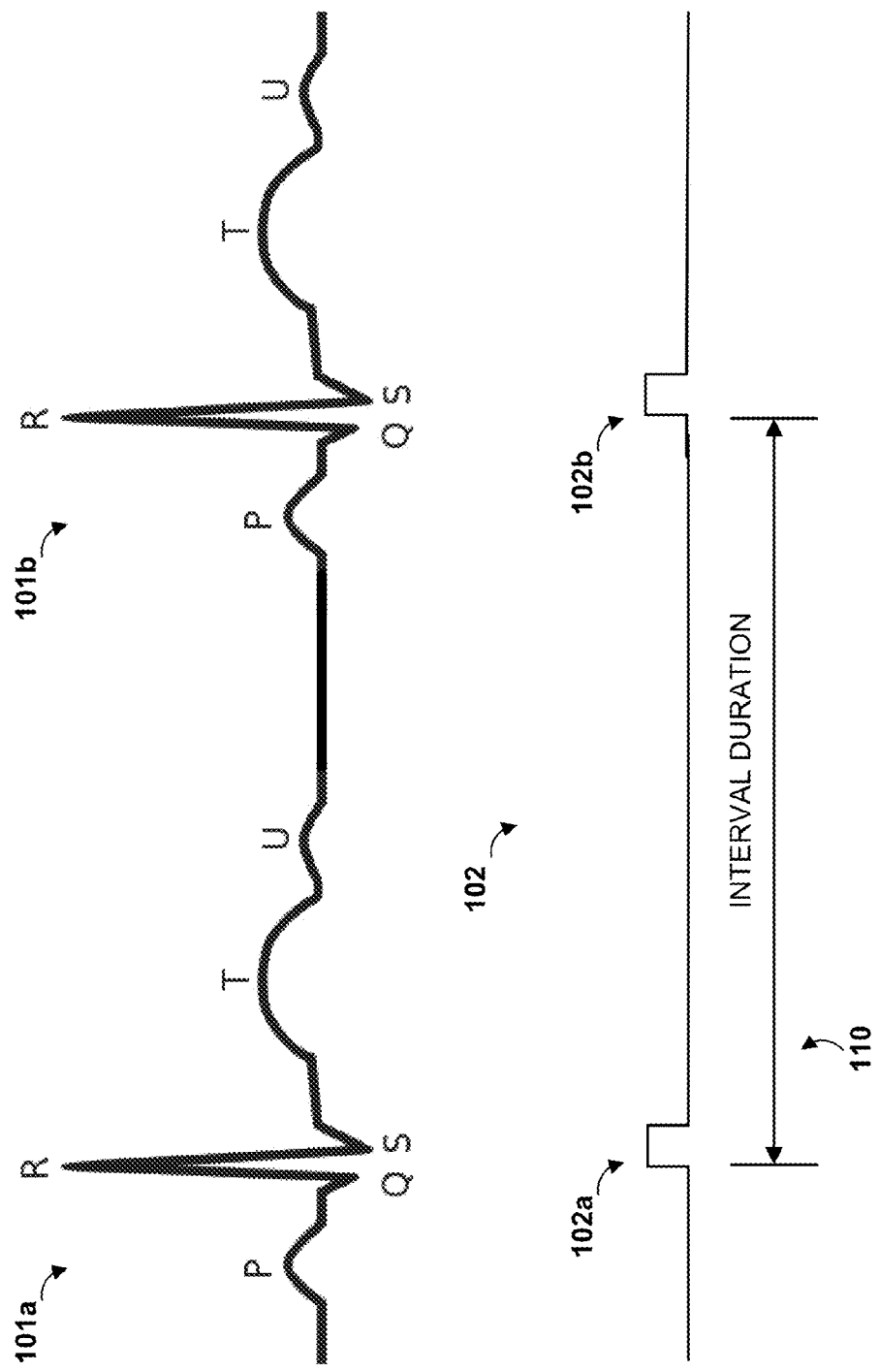
FIG. 7 depicts one example of a heart rate signal created from an ECG signal consistent with this disclosure.

FIG. 7 depicts an example of generation of a heart rate signal 102 indicative of at least one interval duration 110 of cardiac activity in a patient consistent with the disclosure provided herein. FIG. 7 shows two detected sequential cardiac cycles 101a, 101b that each independently represent detected intrinsic depolarization and repolarization of a patient's heart. As discussed above, with respect to FIGS. 3 and 4, IMD 16 may be operable to detect characteristics of an ECG signal (e.g. an R-waves of an ECG signal) and, via one or more sense amplifiers, ADCs, and/or other processing components create a heart rate signal 102 indicative of at least one interval duration 110. For example, as shown in FIG. 7, the heart rate signal 102 indicative of at least one interval duration 110 is a pulse train that includes electrical pulses 102a, 102b, wherein timing of pulses 102a, 102b of the pulse train 102 indicate at least one interval duration 110.

Figure 8:
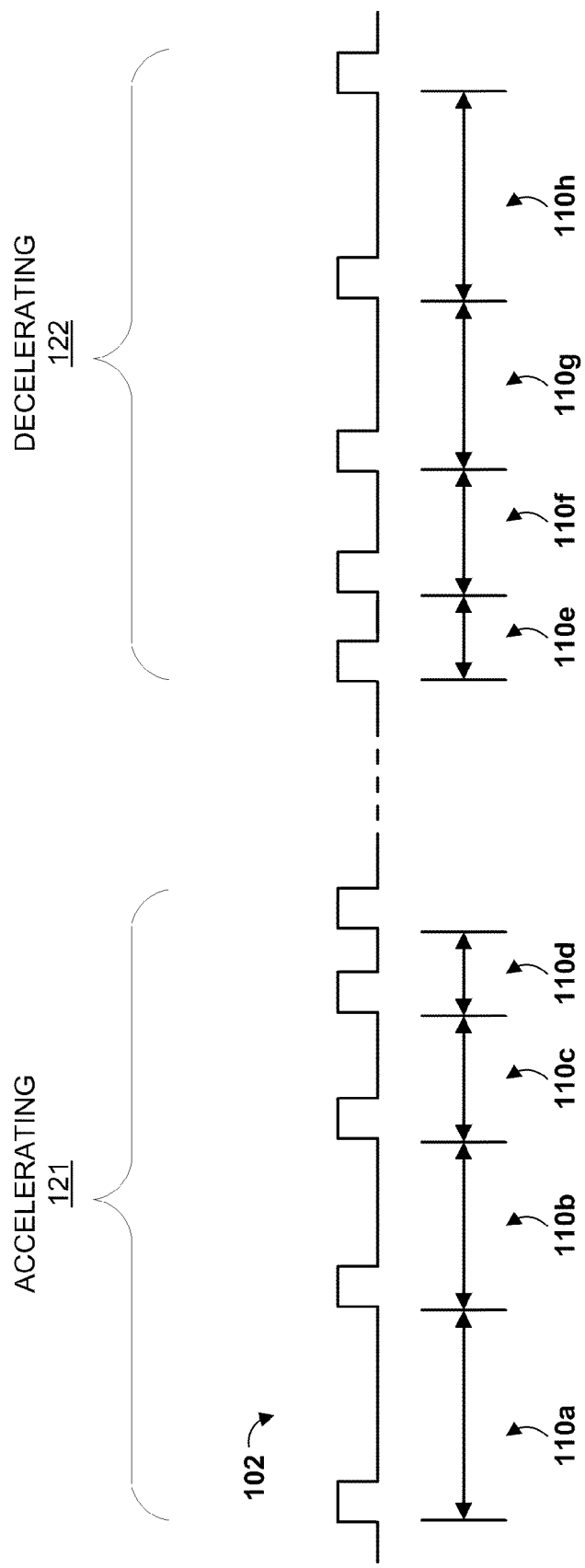
FIG. 8 depicts an example heart rate signal that includes both an accelerating portion and a decelerating portion consistent with this disclosure.

FIG. 8 shows one example heart rate signal 102 that includes indications of interval durations 110a-h. Heart rate signal 102 includes portions of both accelerating 121 and decelerating 122 interval durations 110. As shown in FIG. 8, interval durations 110a-110d are sequentially shorter. Processor 80 may identify accelerating portions 121 of a heart rate signal 102. In one example, processor 80 may identify an accelerating portion 121 of heart rate signal 102 if at least one sequential interval 110 duration is shorter than a previous interval duration 110. Processor 80 may instead identify an accelerating portion 121 of heart rate signal 102 when a predefined number of consecutive interval durations 110 are shorter in time than previous interval durations 110, for example three consecutively shorter interval durations 110. In another example, processor 80 may identify an accelerating HRV portion 121 based on a relative difference between consecutively shorter interval durations 110. For example, processor 80 may identify an accelerating portion 121 when an interval duration 110 is 40% shorter than a previous interval duration 110. In yet another example, processor 80 may identify an accelerating portion 121 when a predefined number of consecutive interval durations 110 are a predefined percentage or predefined time (e.g. clock cycles) shorter than previous interval durations 110. For example, an accelerating portion 121 may be identified when three sequential interval durations 110 are 40% shorter than sequentially previous interval durations 110.

As also shown in FIG. 8, interval durations 110e-110h are sequentially longer. Processor 80 may identify a plurality of interval durations 110e-110h as a decelerating portion 122 of heart rate signal 102 if at least one sequential interval duration 110 is longer than a previous interval duration 110. In one example, processor 80 may instead identify a decelerating portion 122 of heart rate signal 102 when a predefined number of consecutive interval durations 110 are longer in time than previous interval durations 110, for example 3 consecutively longer interval durations. In another example, processor 80 may identify a decelerating portion 122 based on a relative difference between consecutively longer interval durations 110. For example, processor 80 may identify a decelerating portion 122 when an interval duration 110 is 40% longer than a previous interval duration 110. In yet another example, processor 80 may identify a decelerating portion 122 when a predefined number of consecutive interval durations 110 are a predefined percentage or predefined time (e.g. clock cycles)

longer than a previous interval duration 110. For example, a decelerating portion 122 may be identified when three successive interval durations 110 are 40% longer than a previous interval duration 110.

In example illustrated in FIG. 8, the accelerating portion 121 and decelerating portion 122 each comprise a plurality of consecutive interval durations 110 for ease of illustration. In other examples, an accelerating portion or decelerating portion may include any number of, e.g., one or more, intervals. In some examples, accelerating and decelerating portions may alternate on an interval-to-interval basis. In some examples, a heart rate signal analyzed according to the techniques herein may include more than one accelerating portion and/or more than one decelerating portion.

In one example, a medical device adapted to detect indications of cardiac activity to determine one or more interval durations 110 may store interval durations in a memory as they are detected. These stored indications may be later accessed for processing and/or communication.

Figure 9:
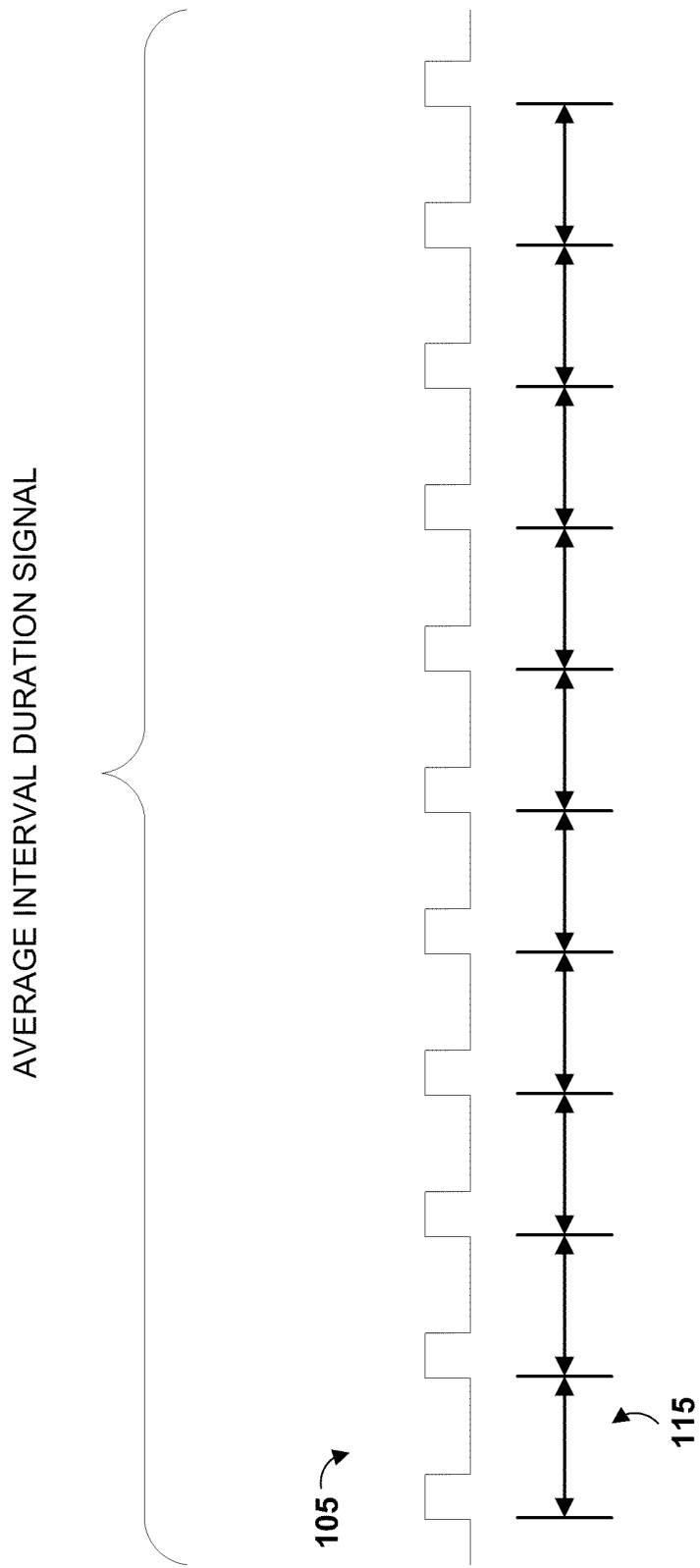
FIG. 9 depicts an average interval duration signal consistent with this disclosure.

FIG. 9 shows one example of an average interval duration signal 105. Processor 80 may calculate, based on one or more heart rate signals 102 that include at least one indication of an interval duration 110, an average interval duration 115 of all the cardiac cycles of a particular time period. Correspondingly, processor 80 may be adapted to generate an average interval duration signal 105 based on the average interval duration 115. The average interval duration signal 105 may be a pulse train including individual pulses, wherein the individual pulses represent an average interval duration 115 of a heart rate signal 102 over a particular time period. In another example, an average interval duration signal 115 may be stored in a memory for later processing and/or communication.

As described below, an average interval duration signal 105 or average interval duration 115 may be utilized according to signal processing techniques consistent with the disclosure provided herein.

Figure 10:
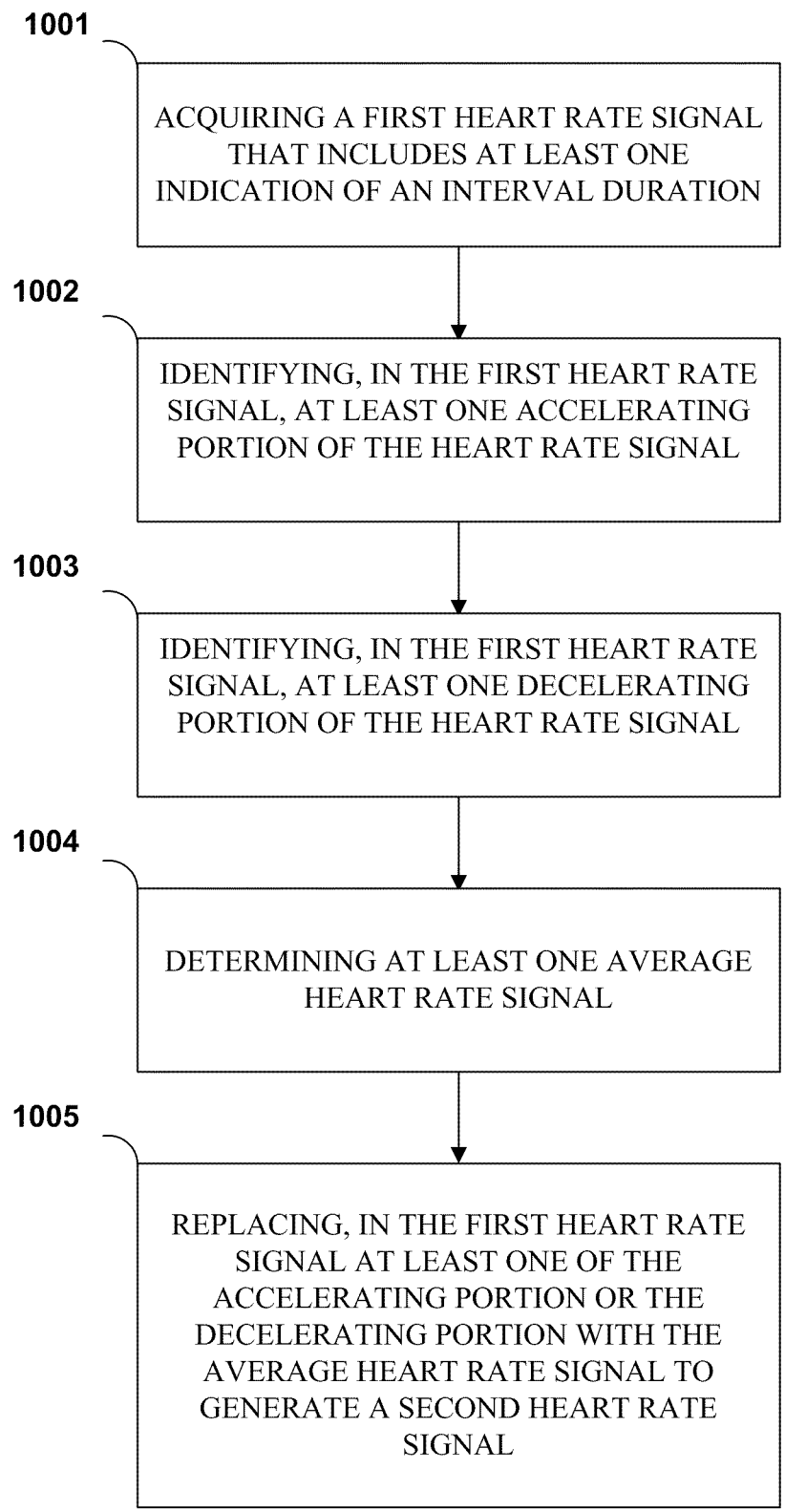
FIG. 10 is a flow diagram that depicts an example method of processing a heart rate signal consistent with this disclosure.

FIG. 10 illustrates generally one example of a method of processing a heart rate signal that includes at least one indication of an interval duration consistent with the disclosure provided herein. The method includes acquiring a first heart rate signal that includes at least one indication of an interval duration (1001). In one example, acquiring the first heart rate signal includes detecting intrinsic electrical depolarization and/or repolarization of at least one cardiac cycle, e.g. an ECG signal detected by sensing of an intrinsic cardiac electrical signal via one or more electrodes. In other examples, acquiring the first heart rate signal may include detecting via one or more pressure sensors, force sensors, flow sensors, audio sensors, or any other sensor capable of detecting cardiac activity. In one example, the at least one interval duration is an R-R interval duration of cardiac cycles. In another example, the at least one interval duration is a P-P interval duration. In one example, the at least one heart rate signal is a pulse train, wherein timing of pulses of the pulse train indicate at least one interval duration. In another example, detected indications of interval durations of intrinsic electrical depolarization and/or repolarization may be stored in a memory for further processing.

The method further includes identifying, in the first heart rate signal, at least one accelerating portion of the heart rate signal (1002). The at least one accelerating portion of the heart rate signal may include at least one interval duration that is shorter than a sequentially previous interval duration. In one example, identifying the at least one accelerating portion includes identifying a predefined number of consecutive interval durations that are shorter than a previous interval duration. In another example, identifying the at least one accelerating portion includes identifying at least one interval duration which is a predefined percentage or duration shorter than a sequentially previous interval duration. In yet another example, identifying the at least one accelerating portion includes identifying a predefined number of interval durations that are a predefined percentage or duration shorter than at least one previous interval duration.

The method further includes identifying, in the first heart rate signal, at least one decelerating portion of the heart rate signal (1003). The at least one decelerating portion of the heart rate signal may include at least one interval duration that is longer than a sequentially previous interval duration. In one example, identifying the at least one decelerating portion includes identifying a predefined number of interval durations that are longer than a previous interval duration. In another example, identifying the at least one decelerating portion includes identifying at least one interval duration which is a predefined percentage or duration longer than a previous interval duration. In yet another example, identifying the at least one decelerating portion includes identifying a predefined number of interval durations that are a predefined percentage or duration longer than a previous interval duration.

The method further includes determining an average heart rate signal or value (1004). In one example, the average heart rate signal is a pulse train with substantially consistent durations between individual pulses of the pulse train. In one example, a time period between individual pulses is indicative of an average interval duration of a patient's heart rate. In one example, determining an average heart rate signal includes monitoring a patient's heart rate to determine an average interval duration of cardiac cycles. In one example, in which detected indications of interval durations of intrinsic electrical depolarization and/or repolarization are stored in a memory, an average heart rate value may be substituted for individual interval durations stored in memory that are identified as accelerating or decelerating interval durations.

The method further includes replacing, in the first heart rate signal at least one of the accelerating portion or the decelerating portion with the average heart rate signal, e.g., replacing the intervals 110 of the accelerating or decelerating portion with the average interval 115, to generate a second heart rate signal (1005). The method may further include acquiring a frequency domain signal of the second heart rate signal. In addition, the method may further include diagnosing and/or predicting one or more autonomic conditions based on processing or analyses of the frequency domain signal of the second heart rate signal.

FIGS. 11A and 11B depict first and second heart rate signals 102 and 108, respectively, consistent with the disclosure provided herein. FIG. 11A depicts a first heart rate signal 102 that includes at least one accelerating portion 121 and at least one decelerating portion 122 identified by brackets. The waveform of FIG. 11A further includes a portion not identified by a bracket that presents substantially constant interval durations 110. Processor 80 may be adapted to identify at least one accelerating portion 121 and at least one decelerating portion 122 of first heart rate signal 102.

FIG. 11B depicts a second heart rate signal 108. As shown, the second heart rate signal 108 includes an average heart rate signal (e.g., average interval duration signal 105 depicted in FIG. 9) 123 substituted for the decelerating portion 122 of the first heart rate signal. Processor 80 may be adapted to substitute the average heart rate signal 123 for the decelerating portion 122 of the first heart rate signal 102 to create an accelerating second heart rate signal 108. As further discussed below with respect to FIGS. 13-16, an accelerating second heart rate signal 108 may be processed and/or analyzed and used to predict or detect one or more autonomic conditions of a patient.

FIGS. 12A and 12B depict first and second heart rate signals 102 and 109, respectively, consistent with the disclosure provided herein. FIG. 12A depicts a first heart rate signal 102 that includes at least one accelerating portion 121 and at least one decelerating portion 122 identified by brackets. The waveform of FIG. 12A further includes a portion not identified by a bracket that presents substantially constant interval durations for a plurality of cardiac cycles. Processor 80 may identify the at least one accelerating portion 121 and at least one decelerating portion 122 of first heart rate signal 102.

FIG. 12B depicts a second heart rate signal 109. As shown, second heart rate signal 109 includes an average heart rate signal 123 (e.g average interval duration signal 105 depicted in FIG. 9) substituted for the accelerating portion 121 of the first heart rate signal 102. Processor 80 may substitute the average heart rate signal 123 for the accelerating portion 121 of the first heart rate signal 102 to create a decelerating second heart rate signal 109. As further discussed below with respect to FIGS. 13-16, decelerating second heart rate signal 109 may be processed and/or analyzed and used to predict or detect one or more autonomic conditions.

FIG. 13 depicts an example frequency domain signal 132 of a heart rate signal, e.g. heart rate signal 102 as shown in FIGS. 11A-B and 12A-B. Such a frequency domain signal 132 may be referred to as an autonomic tone signal. Processor 80 may acquire frequency domain signal 132 by performing one or more transform operations on a heart rate signal 102, e.g. a Fourier transform. The illustrated example frequency domain signal 132 illustrates power within a plurality of discrete frequency bands, which may be determined by integrating values of a signal provided by such a transform within the frequency bands. In other examples, any signal processing techniques may be used to derive a frequency domain signal that indicates the signal power of a heart rate signal as a function of frequency from the heart rate signal. In general, frequency domain signal 132 may include one or more indications of frequencies of a patient's heart rate.

As depicted in FIG. 13, a frequency domain signal 132 of a patient's heart rate signal 102 may show frequencies at which cardiac contractions occur. As also shown, a particular frequency may occur during both accelerating portions 121 and decelerating portions 122 of a heart rate signal 102. As such, isolated analysis of a frequency spectrum of either accelerating portions 121 or decelerating portions 122 may be difficult if not impossible to achieve, thus preventing or limiting analysis and/or processing of certain HRV characteristics of a heart rate signal 102.

Figure 14:
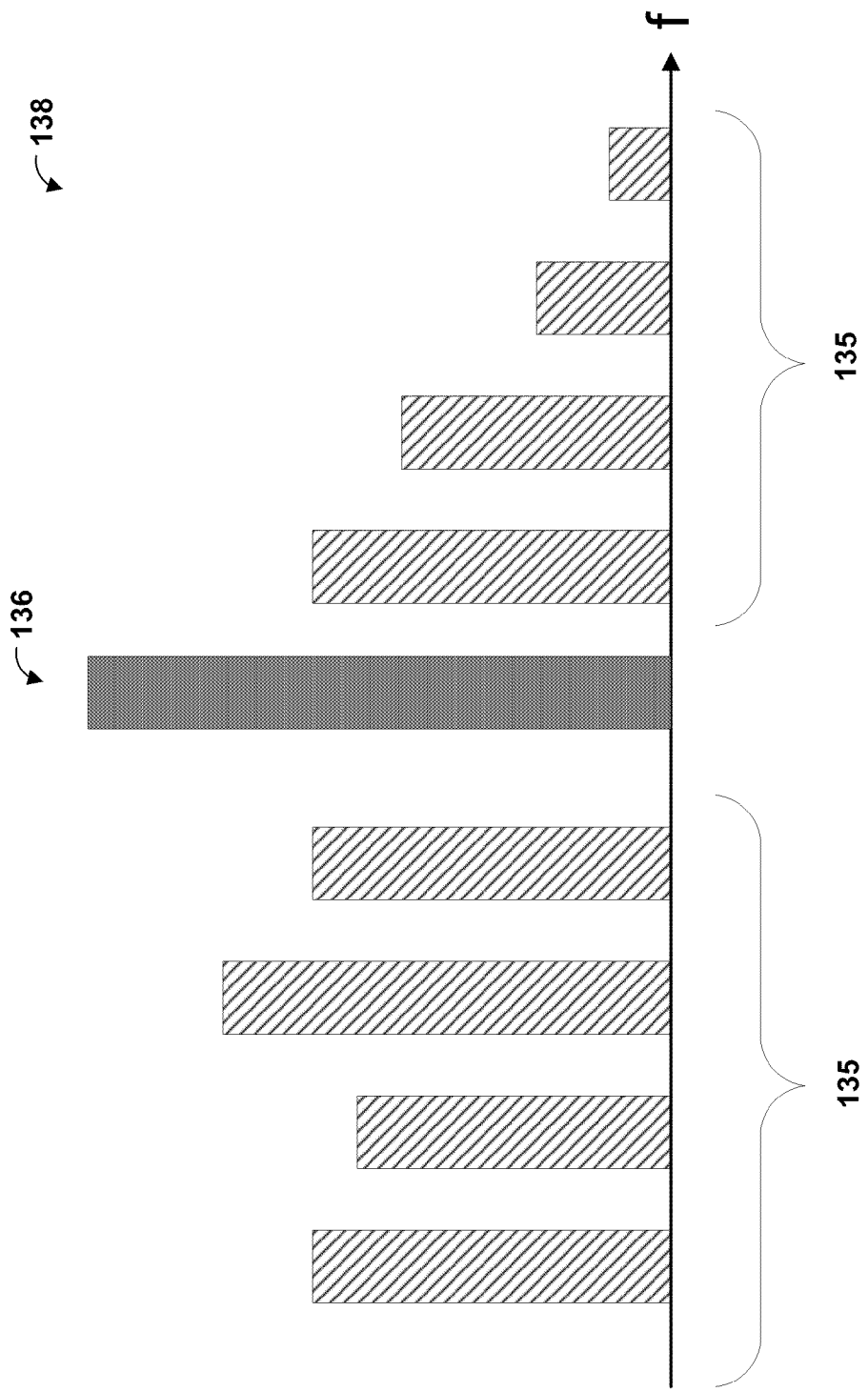
FIG. 14 depicts an example frequency response of an accelerating second heart rate signal consistent with this disclosure.

FIG. 14 depicts frequency domain signal 138. Frequency domain signal 138 is a frequency response of a second heart rate signal such as second heart rate signal 108 depicted in FIG. 11B, wherein decelerating portions 122 of a first heart rate signal have been replaced with an average heart rate signal 123. As shown, frequency domain signal 138 depicts a plurality of frequencies present in second heart rate signal 108. For example, frequency domain signal 138 includes frequencies 135 that represent accelerating portions 121 of heart rate signal 108. Frequency domain signal 138 further includes frequencies 136 that represent a frequency of average heart rate signal 123. For example, frequencies 136 may be from substantially non-accelerating/decelerating portions of heart rate signal 102/108. Frequencies 136 may also or instead represent average heart rate signal 123, which was substituted for decelerating portions 122 of first heart rate signal 102 to create second heart rate signal 108.

Analyzing and/or further processing of frequency domain signal 138 may enable improved analysis of acceleration-related HRV characteristics. For example, in contrast with frequency domain signal 132 depicted in FIG. 13, signal 138 does not include frequency information from decelerating portions 122 of heart rate signal 102. Thus, a frequency spectrum of only accelerating portions 121 of heart rate signal 102 may be analyzed and/or processed independently.

Further, because a frequency of an average heart rate signal 123 is known, analysis of frequencies of accelerating portions 121 of heart rate signal 102 may be further isolated. For example, a frequency of average heart rate signal 123 may be filtered (e.g. narrow band filter) or otherwise removed from frequency domain signal 138. Also, because average heart rate signal represents an average interval duration, filtering the frequency of average heart rate signal 123 may further remove from frequency domain signal 138 frequencies of non-accelerating or non-decelerating portions of heart rate signal 102, thus further isolating the frequency response of accelerating portions 121 of heart rate signal 102.

Figure 15:
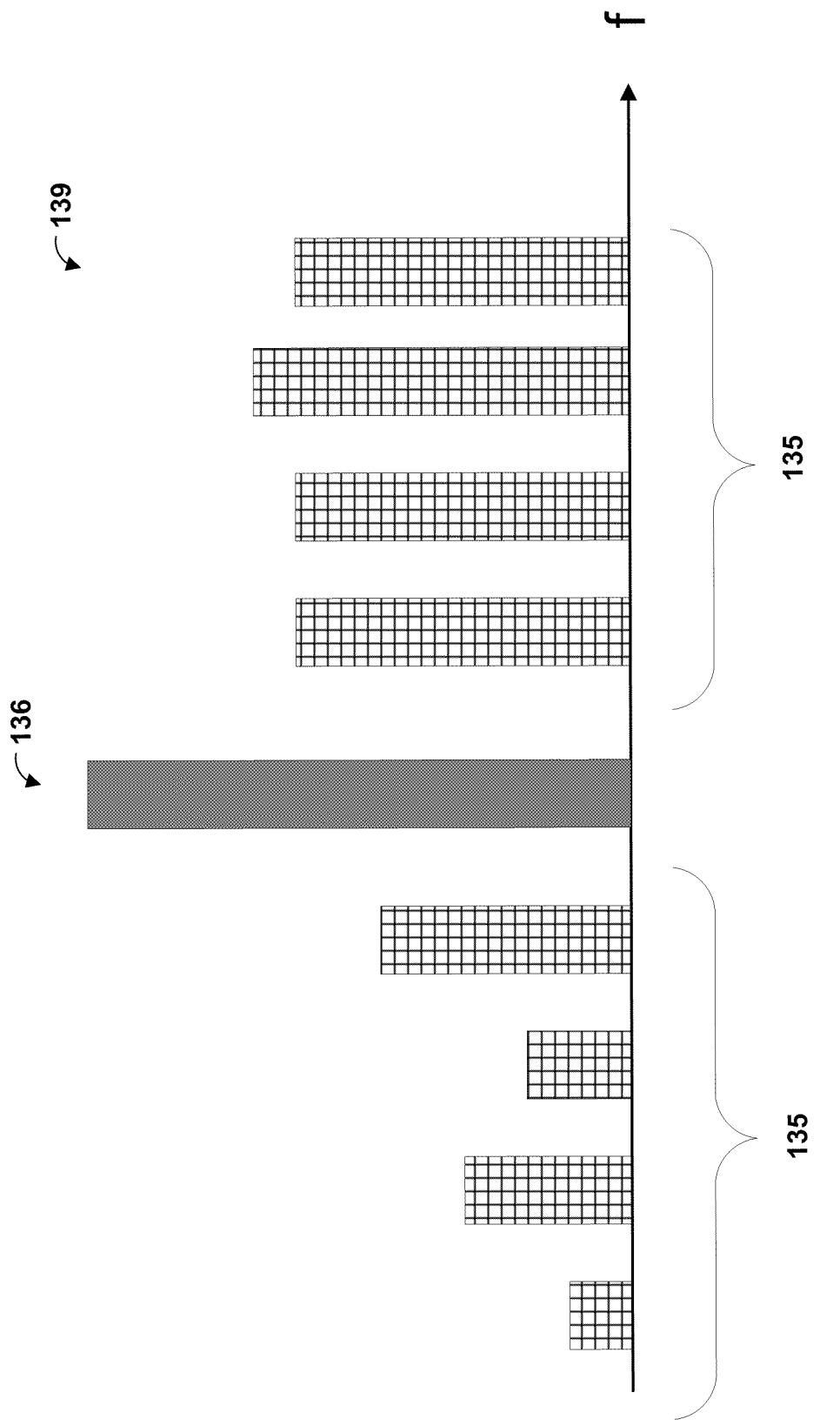
FIG. 15 depicts an example frequency response of a decelerating second heart rate signal consistent with this disclosure.

FIG. 15 depicts frequency domain signal 139. Frequency domain signal 139 is a frequency response of a second heart rate signal such as second heart rate signal 109 as depicted in FIG. 12B, wherein accelerating portions 121 of a first heart rate signal 102 have been replaced with an average heart rate signal 123. As shown, frequency domain signal 139 depicts a plurality of frequencies present in second heart rate signal 109. For example, frequency domain signal 139 includes frequencies 135 that represent decelerating portions of heart rate signal 109. Frequency domain signal 139 further includes frequencies 136 that represent a frequency of average heart rate signal 123. For example, frequencies 136 may be from substantially non-accelerating/decelerating portions of heart rate signal 102/109. Frequencies 136 may also or instead represent average heart rate signal 123, which was substituted for accelerating portions 121 of first heart rate signal 102 to create second heart rate signal 109.

Analyzing and/or further processing of frequency domain signal 139 may enable improved analysis of deceleration-related HRV characteristics. For example, in contrast with frequency domain signal 132 depicted in FIG. 13, signal 139 does not include frequency information from accelerating portions 121 of heart rate signal 102. Thus, a frequency spectrum of only decelerating portions 122 of heart rate signal 102 may be analyzed and/or further processed independently.

Further, because a frequency of an average heart rate signal 123 is known, analysis of frequencies of decelerating portions 122 of heart rate signal 102 may be further isolated. For example, a frequency of average heart rate signal 123 may be filtered (e.g. narrow band filter) or otherwise removed from frequency domain signal 139. Also, because average heart rate signal represents an average interval duration, filtering the frequency of average heart rate signal 123 may further remove from frequency domain signal 138 frequencies of non-accelerating or non-decelerating portions of heart rate signal 102, thus further isolating the frequency response of decelerating portions 122 of heart rate signal 102.

Figure 16:
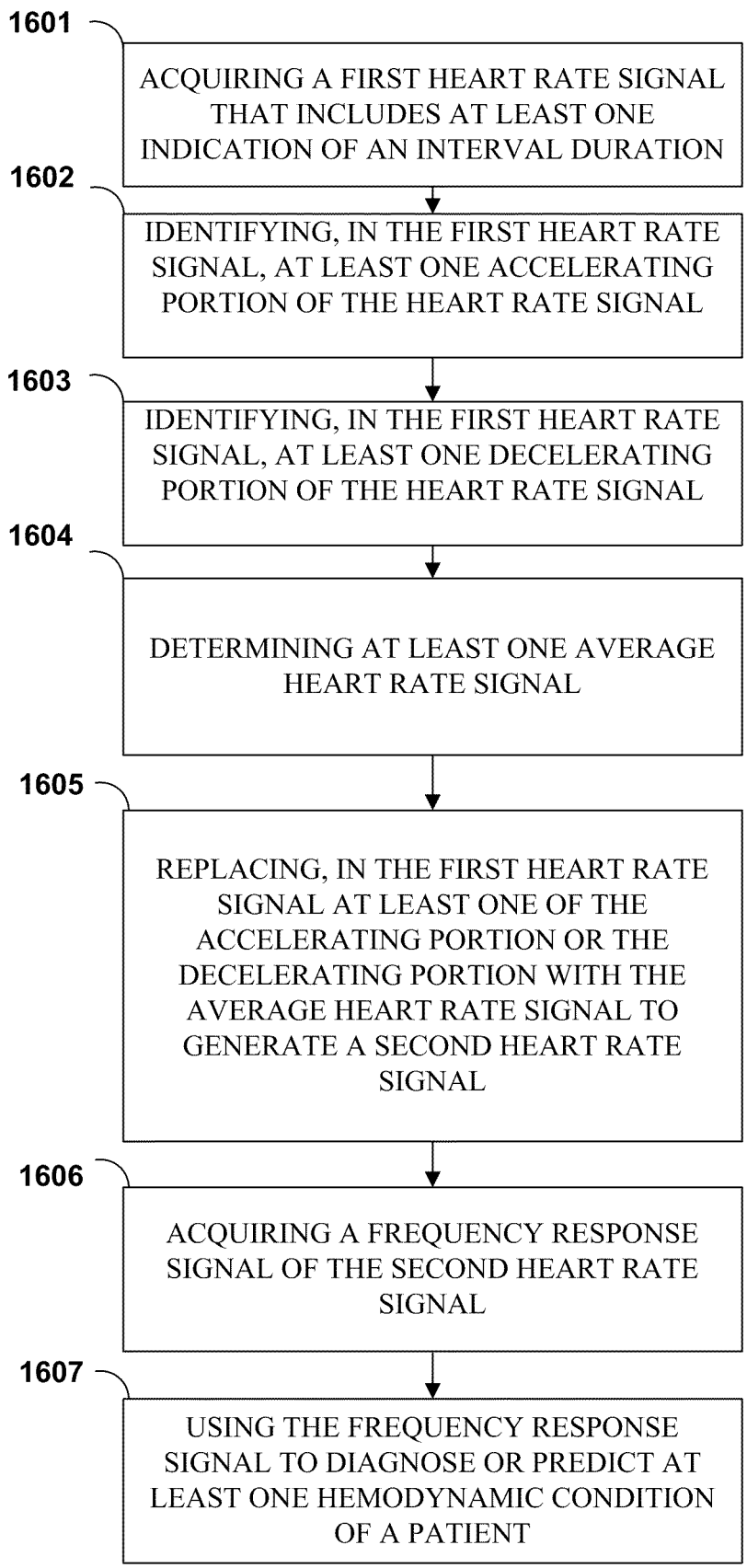
FIG. 16 is a flow diagram of an example method of processing a heart rate signal to diagnose or predict one or more autonomic conditions of a patient consistent with this disclosure.

FIG. 16 is a flow chart diagram that depicts one example of a method of detecting an autonomic condition of a patient. The method includes acquiring a first heart rate signal that includes at least one indication of an interval duration (1601). The method further includes identifying, in the first heart rate signal, at least one accelerating portion of the heart rate signal (1602). The method further includes identifying, in the first heart rate signal, at least one decelerating portion of the heart rate signal (1603). The method further includes determining an average heart rate signal (1604). The method further includes replacing, in the first heart rate signal at least one of the accelerating portion or the decelerating portion with the average heart rate signal to generate a second heart rate signal (1605). Where the method includes replacing the accelerating portion with the average heart rate signal, a decelerating second heart rate signal is generated. Where the method includes replacing the decelerating portion with the average heart rate signal, an accelerating second heart rate signal is generated.

The method further includes acquiring a frequency response signal of the second heart rate signal (1606). In one example, the frequency response signal of the second heart rate signal is acquired by performing a transform operation on the second heart rate signal. The method further includes diagnosing or predicting at least one autonomic condition of a patient based on the frequency response of the second heart rate signal (1607)

In one example, diagnosing or predicting at least one autonomic condition of the patient includes estimating sympathetic or parasympathetic modulation. In one example, diagnosing or predicting at least one autonomic condition of the patient includes analyzing one or more low frequency (e.g. frequencies less than 0.15 Hz) portions of the frequency response signal to estimate sympathetic modulation. In one example, a detected increase in sympathetic tone may be utilized to predict a ventricular tachyarrhythmia. In another example, diagnosing or predicting at least one autonomic condition of the patient includes analyzing one or more high frequency portions (e.g. frequencies greater than 0.15 Hz) of the frequency response signal to estimate parasympathetic modulation. In one example, a detected decrease in parasympathetic tone may be used as an indicator to predict a ventricular tachyarrhythmia.

In some examples, both an accelerating second heart rate signal and a decelerating second heart rate signal are generated. In such examples, respective frequency peaks representing the sympathetic and parasympathetic components may be identified and, in some examples, a ratio between these peaks may be determined to evaluate autonomic balance. In various examples, the method may further include initiating and/or titrating one or more therapies in response to diagnosis or prediction of one or more autonomic conditions, such as autonomic disbalance. Examples of therapies that may be initiated and/or titrated may include, alone or in combination, cardiac stimulation (e.g. electrical stimulation), spinal cord stimulation, vagal stimulation, vagal branch stimulation, AV nodal stimulation, and/or fat pad stimulation (e.g., AV nodal fat pad stimulation). In another example, various drug delivery therapies may be initiated or titrated in response to diagnosis or prediction of one or more autonomic conditions, e.g. delivery of anti-inflammatory medication via one or more drug pumps.

In one example, where a ventricular tachyarrhythmia is predicted or detected, a processor or device may initiate overdrive pacing, anti-tachycardia pacing, spinal cord stimulation, vagal stimulation, vagal branch stimulation, AV nodal stimulation, and/or fat pad stimulation (e.g., AV nodal fat pad stimulation) to avoid the predicted tachyarrhythmia.

In one example, diagnosing or predicting at least one autonomic condition of the patient includes diagnosing or predicting atrial arrhythmia in the patient. In some examples, the method may include providing one or more therapies in response to predicting the occurrence of an arrhythmia. For example, IMD 16 may initiate overdrive pacing in one or more atria and/or ventricles of heart 12. As another example, IMD 16 may deliver antitachycardia pacing in response to predicting the occurrence of an arrhythmia. In examples in which IMD 16 is configured to deliver neuro stimulation, IMD 16 may deliver stimulation signals to or proximate to the spinal cord, vagus nerve, or other neural targets to help adjust autonomic activity. The therapy that IMD 16 delivers in response to predicting the occurrence of an arrhythmia may be configured to help prevent the predicted arrhythmia from occurring.

Figure 17:
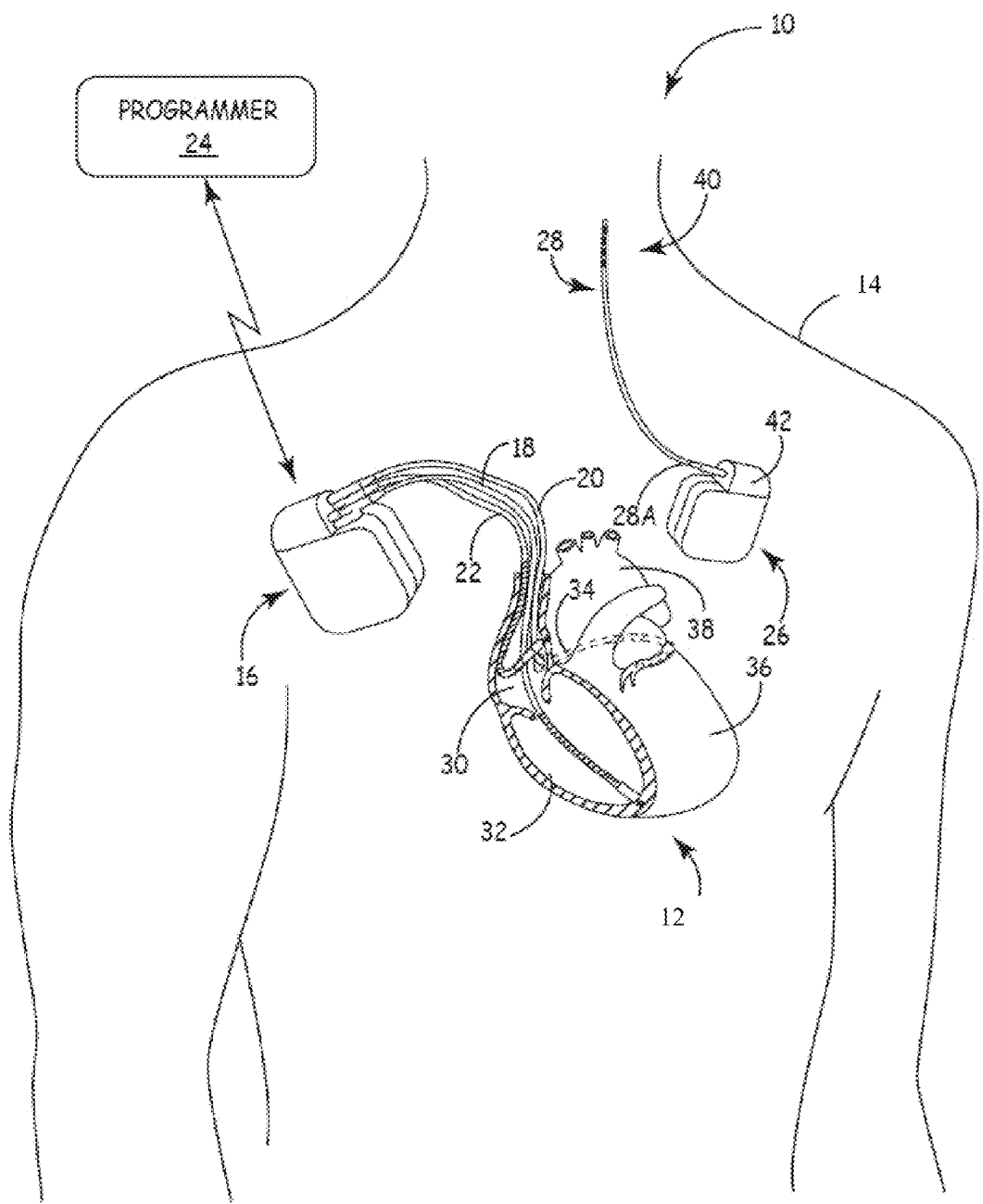
FIG. 17 depicts one specific example of a therapy system that provides both cardiac and nerve stimulation therapies consistent with this disclosure.

FIG. 17 is a conceptual drawing illustrating an example system 10 that includes IMD 16 and IMD 26. In the example of FIG. 17, IMD 16 may be an implantable cardiac device, such as a cardiac monitoring device or an implantable pacemaker, cardioverter, and/or defibrillator. As described with respect to system 10 of FIG. 1, IMD 16 may monitor signals from and, in some examples, deliver electrical signals to heart 12. In the example of FIG. 17, IMD 26 may be a neurostimulator that delivers electrical stimulation to and/or monitors conditions associated with the brain, spinal cord, or neural tissue of patient 14. In the example of FIG. 17, IMD 26 is implanted in patient 14 proximate to target stimulation site 40, such as a tissue site proximate a vagus nerve. More particularly, lead 28 is coupled to IMD 26 and extends from IMD 26 to target stimulation site 40. Lead 28 may include one or more electrodes to sense signals from and/or deliver electrical signals to target stimulation site 40. In other examples, IMD 26 is positioned to deliver neurostimulation to another target stimulation site, such as the brain or spinal cord. Accordingly, where a medical system such as system 10 of FIG. 17 is employed, one or more combinations of cardiac and neural stimulation may be provided in response to a detected or predicted autonomic condition.

Various examples have been described. These and other examples are within the scope of the following claims. Although described herein as implemented by an IMD and system including an IMD, in other examples, the techniques described herein may be implemented in an external medical device.

In addition, it should be noted that therapy system 10 may not be limited to treatment of a human patient. In alternative examples, therapy system 10 may be implemented in non-human patients, e.g., primates, canines, equines, pigs, and felines. These other animals may undergo clinical or research therapies that my benefit from the subject matter of this disclosure.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A method, comprising:
acquiring a first heart rate signal that includes an indication of at least one interval duration of a heart rate of a patient;
identifying at least one accelerating portion of the first heart rate signal for which the heart rate is increasing;
identifying at least one decelerating portion of the first heart rate signal for which the heart rate is decreasing;
determining an average heart rate signal; and
replacing, in the first heart rate signal, one of only the accelerating portion or only the decelerating portion with the average heart rate signal to produce a second heart rate signal such that the second heart rate signal is one of an accelerating signal when only the decelerating portion is replaced and a decelerating signal when only the accelerating portion is replaced.

2. The method of claim 1, wherein acquiring the first heart rate signal comprises:
acquiring a cardiac electrical signal; and
analyzing the cardiac electrical signal to determine the at least one interval duration.

3. The method of claim 1, wherein acquiring the first heart rate signal comprises:
acquiring the first heart rate signal based on at least one signal selected from the group consisting of:
a pressure signal;
an audio signal;
a force signal; and
a motion signal.

4. The method of claim 1, further comprising acquiring a frequency response of the second heart rate signal.

5. The method of claim 4, further comprising filtering the frequency response of the second heart rate signal to remove one or more frequencies associated with the average heart rate signal.

6. The method of claim 4, further comprising diagnosing or predicting at least one autonomic condition of a patient based on the frequency response of the second heart rate signal.

7. The method of claim 6, further comprising responding to the diagnosis or prediction of at least one autonomic condition of a patient by initiating or modifying at least one therapy selected from the group consisting of:
overdrive pacing;
anti-tachycardia pacing;
spinal stimulation;
vagal stimulation;
vagal branch stimulation;
AV nodal stimulation;
fat pad stimulation; and
drug delivery therapy.

8. The method of claim 6, wherein diagnosing or predicting at least one autonomic condition of a patient based on the frequency response of the second heart rate signal includes estimating sympathetic or parasympathetic modulation.

9. The method of claim 6, wherein diagnosing or predicting at least one autonomic condition of a patient based on the frequency response of the second heart rate signal includes diagnosing or predicting a tachyarrhythmia in the patient.

10. The method of claim 6, wherein diagnosing or predicting at least one autonomic condition of a patient based on the frequency response of the second heart rate signal includes diagnosing or predicting the development of cardiovascular disease in the patient.

11. The method of claim 9, wherein replacing, in the first heart rate signal, one of the accelerating portion or the decelerating portion with the average heart rate signal to produce a second heart rate signal comprises:
replacing, in the first heart rate signal, the accelerating portion with the average heart rate signal to produce a decelerating second heart rate signal indicative of the decelerating portion of the first heart rate signal; and
predicting a ventricular tachyarrhythmia based on the frequency response of the decelerating second heart rate signal.

12. The method of claim 1, further comprising:
replacing, in the first heart rate signal, the accelerating portion with the average heart rate signal to produce a decelerating second heart rate signal;
replacing, in the first heart rate signal, the decelerating portion with the average heart rate signal to produce an accelerating second heart rate signal;
acquiring a frequency response of the decelerating second heart rate signal;
acquiring a frequency response of the accelerating second heart rate signal; and
diagnosing or predicting one or more autonomic conditions based on the frequency response of the decelerating second heart rate signal and the frequency response of the accelerating second heart rate signal.

13. The method of claim 12, wherein diagnosing or predicting one or more autonomic conditions based on the frequency response of the decelerating second heart rate signal and the frequency response of the accelerating second heart rate signal comprises estimating a ratio between sympathetic and parasympathetic modulation based on the frequency response of the decelerating second heart rate signal and the frequency response of the accelerating second heart rate signal.

14. A system, comprising:
a medical device;
at least one sensor coupled to the medical device that detects at least one indication of a cardiac cycle of a patient; and
a processor configured to:
acquire, based on detection by the sensor of at least one indication of a cardiac cycle, at least one first heart rate signal that includes at least one indication of an interval duration;
identify at least one accelerating portion of the first heart rate signal for which the heart rate is increasing;
identify at least one decelerating portion of the first heart rate signal for which the patient's heart rate is decreasing;
determine an average heart rate signal; and
replace, in the first heart rate signal, one of only the accelerating portion or only the decelerating portion with the average heart rate signal to produce a second heart rate signal such that the second heart rate signal is one of an accelerating signal when only the decelerating portion is replaced and a decelerating signal when only the accelerating portion is replaced.

15. The system of claim 14, wherein the processor is configured to acquire a cardiac electrical signal and analyze the cardiac electrical signal to determine the at least one interval duration to acquire the first heart rate signal.

16. The system of claim 14, wherein the processor is further configured to acquire a frequency response of the second heart rate signal.

17. The system of claim 16, wherein the processor is further configured to filter the frequency response of the second heart rate signal to remove one or more frequencies associated with the average heart rate signal.

18. The system of claim 16, wherein the processor is further configured to diagnose or predict at least one autonomic condition of a patient based on the frequency response of the second heart rate signal.

19. The system of claim 18, wherein the processor is further configured to respond to the diagnosis or prediction of at least one autonomic condition of a patient by initiating or modifying at least one therapy selected from the group consisting of:
  overdrive pacing;
  anti-tachycardia pacing;
  spinal stimulation;
  vagal stimulation;
  vagal branch stimulation;
  AV nodal stimulation;
  fat pad stimulation; and
  drug delivery therapy.

20. The system of claim 18, wherein the processor is further configured to estimate sympathetic or parasympathetic modulation to diagnose or predict at least one autonomic condition of a patient based on the frequency response of the second heart rate signal.

21. The system of claim 18, wherein the processor is further configured to diagnose or predict a tachyarrhythmia in the patient based on the frequency response of the second heart rate signal.

22. The system of claim 14, wherein the processor is further configured to:
  replace, in the first heart rate signal, the accelerating portion with the average heart rate signal to produce a decelerating second heart rate signal;
  replace, in the first heart rate signal the decelerating portion with the average heart rate signal to produce an accelerating second heart rate signal;
  acquire a frequency response of the decelerating second heart rate signal;
  acquire a frequency response of the accelerating second heart rate signal; and
  diagnose or predict one or more autonomic conditions based on the frequency response of the decelerating second heart rate signal and the frequency response of the accelerating second heart rate signal.

23. The system of claim 22, wherein the processor is further configured to:
  diagnose or predict one or more autonomic conditions based on the frequency response of the decelerating second heart rate signal and the frequency response of the accelerating second heart rate signal by estimating a ratio between sympathetic and parasympathetic modulation based on the frequency response of the decelerating second heart rate signal and the frequency response of the accelerating second heart rate signal.

24. The system of claim 14, wherein the medical device is an implantable medical device, and wherein the at least one sensor coupled to the medical device is an electrode that senses a cardiac electrical signal.

25. The system of claim 14, wherein the processor comprises a processor of the medical device.

26. A computer-readable medium comprising instructions for causing a programmable processor to:
  acquire a first heart rate signal that includes an indication of at least one interval duration of a heart rate of a patient;
  identify at least one accelerating portion of the first heart rate signal for which the heart rate is increasing;
  identify at least one decelerating portion of the first heart rate signal for which the heart rate is decreasing;
  determine an average heart rate signal; and
  replace, in the first heart rate signal, one of only the accelerating portion or only the decelerating portion with the average heart rate signal to produce a second heart rate signal such that the second heart rate signal is one of an accelerating signal when only the decelerating portion is replaced and a decelerating signal when only the accelerating portion is replaced.

27. A system, comprising:
  means for detecting at least one indication of a cardiac cycle of a patient;
  means for acquiring, based on detection of at least one indication of a cardiac cycle, at least one first heart rate signal that includes at least one indication of an interval duration;
  means for identifying at least one accelerating portion of the first heart rate signal for which the heart rate is increasing;
  means for identifying at least one decelerating portion of the first heart rate signal for which the patient's heart rate is decreasing;
  means for determining an average heart rate signal; and
  means for replacing, in the first heart rate signal, one of only the accelerating portion or only the decelerating portion with the average heart rate signal to produce a second heart rate signal such that the second heart rate signal is one of an accelerating signal when only the decelerating portion is replaced and a decelerating signal when only the accelerating portion is replaced.

* * * * *